United States Patent
Dziubak et al.

(10) Patent No.: US 11,074,694 B2
(45) Date of Patent: Jul. 27, 2021

(54) IMAGE PROCESSING APPARATUS, OPTICAL COHERENCE TOMOGRAPHY APPARATUS, IMAGE PROCESSING METHOD, AND COMPUTER-READABLE MEDIUM

(71) Applicant: CANON KABUSHIKI KAISHA, Tokyo (JP)

(72) Inventors: Tomasz Dziubak, Torun (PL); Yasuhisa Inao, Tokyo (JP); Marek Rozanski, Toruń (PL); Tomasz Bajraszewski, Głogowo (PL)

(73) Assignee: CANON KABUSHIKI KAISHA, Tokyo (JP)

( * ) Notice: Subject to any disclaimer, the term of this patent is extended or adjusted under 35 U.S.C. 154(b) by 23 days.

(21) Appl. No.: 16/118,591

(22) Filed: Aug. 31, 2018

(65) Prior Publication Data

US 2019/0073776 A1 Mar. 7, 2019

(30) Foreign Application Priority Data

Sep. 4, 2017 (JP) .............................. JP2017-169235

(51) Int. Cl.
*G06K 9/00* (2006.01)
*G06T 7/136* (2017.01)
(Continued)

(52) U.S. Cl.
CPC .............. *G06T 7/136* (2017.01); *A61B 3/102* (2013.01); *G06T 7/194* (2017.01); *G06T 2207/10101* (2013.01)

(58) Field of Classification Search
CPC ..... A61B 3/102; A61B 3/0025; A61B 3/1233; A61B 5/0066; A61B 5/7203;
(Continued)

(56) References Cited

U.S. PATENT DOCUMENTS 9,839,351 B2 * 12/2017 Goto ...................... A61B 3/102
9,883,810 B2 2/2018 Jia et al.
(Continued)

FOREIGN PATENT DOCUMENTS

| JP | 2015511146 A | 4/2015 |
|---|---|---|
| JP | 2016202900 A | 12/2016 |
| WO | 2013116689 A1 | 8/2013 |

OTHER PUBLICATIONS

Spaide, Richard F., James G. Fujimoto, and Nadia K. Waheed. "Image artifacts in optical coherence angiography." Retina (Philadelphia, Pa.) 35.11 (2015): 2163. (Year: 2015).*

(Continued)

*Primary Examiner* — Li Liu
(74) *Attorney, Agent, or Firm* — Rossi, Kimms & McDowell LLP

(57) ABSTRACT

An image processing apparatus includes an acquisition unit that acquires a plurality of pieces of tomographic data indicating tomographic information on substantially the same part of a subject to be inspected, a threshold calculation unit that calculates a threshold from tomographic data associated with a target pixel for which motion contrast data is to be calculated of the plurality of pieces of tomographic data, and a pixel value calculation unit that calculates the pixel value of the target pixel of a motion contrast image based on the threshold and the motion contrast data calculated from the tomographic data associated with the target pixel.

24 Claims, 16 Drawing Sheets

(51) Int. Cl.
*A61B 3/10* (2006.01)
*G06T 7/194* (2017.01)

(58) Field of Classification Search
CPC ........ A61B 5/7207; G06T 2207/10101; G06T 2207/30041; G06T 2207/30101; G06T 7/0016; G06K 2209/05; G06K 9/0061
See application file for complete search history.

(56) References Cited

U.S. PATENT DOCUMENTS

| | | | | |
|---|---|---|---|---|
| 2014/0073917 | A1* | 3/2014 | Huang | A61B 5/7246 600/427 |
| 2014/0160487 | A1 | 6/2014 | Huang | |
| 2014/0221827 | A1* | 8/2014 | Motaghiannezam | G01N 21/4795 600/425 |
| 2014/0228681 | A1 | 8/2014 | Jia et al. | |
| 2016/0317018 | A1* | 11/2016 | Sakagawa | A61B 3/102 |
| 2017/0000327 | A1 | 1/2017 | Fingler | |
| 2017/0065170 | A1 | 3/2017 | Yamashita | |
| 2017/0169590 | A1* | 6/2017 | Huang | G06T 5/002 |
| 2017/0262988 | A1* | 9/2017 | Ikegami | A61B 3/0025 |
| 2017/0319060 | A1* | 11/2017 | Huang | A61B 3/1233 |
| 2018/0020909 | A1* | 1/2018 | Jia | A61B 3/1233 351/206 |
| 2018/0199806 | A1* | 7/2018 | Dziubak | A61B 3/0025 |
| 2018/0263485 | A1* | 9/2018 | Takahashi | A61B 3/0025 |

OTHER PUBLICATIONS

Extended European Search Report issued in European Appln. No. 18191907.7 dated Jan. 28, 2019.
Office Action issued in Japanese Appln. No. 2017-169235 dated Jun. 3, 2021 English machine translation provided.

* cited by examiner

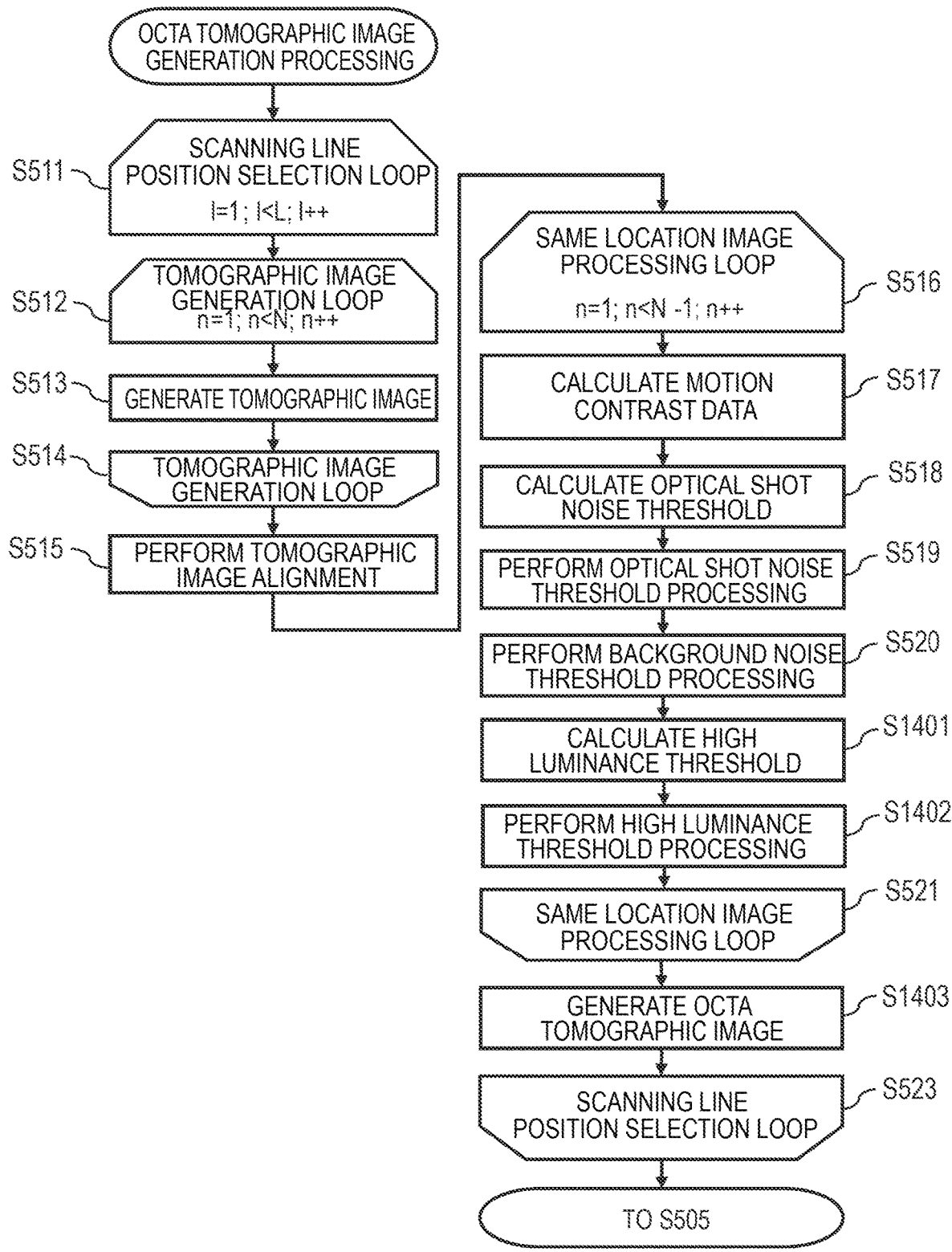

IMAGE PROCESSING APPARATUS, OPTICAL COHERENCE TOMOGRAPHY APPARATUS, IMAGE PROCESSING METHOD, AND COMPUTER-READABLE MEDIUM

BACKGROUND OF THE INVENTION

Field of the Invention

The present invention relates to an image processing apparatus, an optical coherence tomography apparatus, an image processing method, and a computer-readable medium.

Description of the Related Art

In ophthalmology, apparatuses (OCT apparatuses) based on optical coherence tomography (OCT) that enables non-invasive tomographic observation and measurement of a fundus and an anterior eye portion have become popular. The OCT apparatus acquires tomographic information on an eye to be inspected from interference light obtained by irradiating the eye to be inspected with low coherent light (measuring light) and multiplexing return light from the eye to be inspected with reference light. The OCT apparatus can acquire tomographic images of the fundus by scanning the fundus of the eye to be inspected with the low coherent light. In the medical field, the OCT apparatuses are widely used for various purposes from research to clinical.

OCT is generally classified into two types: time-domain OCT and Fourier-domain OCT. Fourier-domain OCT is further classified into spectral-domain OCT (SD-OCT) and swept-source OCT (SS-OCT). Fourier-domain OCT uses a light source having a wide wavelength band. In Fourier-domain OCT, signals are acquired by dispersing interference light, and tomographic information on the subject to be inspected can be acquired by performing Fourier transformation or the like on the acquired signals. In SD-OCT, light is spatially dispersed by a spectroscope. On the other hand, in SS-OCT, a light source that emits light whose wavelength varies with time is used to temporally disperse light.

More recently, it has been feasible to generate an image of the blood flow in the fundus from such a tomographic image and acquire an image similar to those acquired in the conventional fluorescence fundus imaging. Such an image is generally referred to as an OCT angiographic (OCTA) image.

To generate an OCTA image, a plurality of tomographic images of the same part is captured, and an image representing the change in luminance value at the same pixel (target pixel) location between the captured tomographic images is generated. It is known that the luminance of the interior of a blood vessel changes between tomographic images captured at different times since the positions of blood cells in the blood vessel change. The change in luminance value can be determined in various calculation methods, for example, as one of the decorrelation value, the variance and the minimum value divided by the maximum value of the luminance values of the target pixels in two tomographic images captured in a predetermined time. The change in luminance value may be determined by calculating the change in luminance value at the same location between two tomographic images captured in a predetermined time for a plurality of tomographic images and taking an average of the calculated changes in luminance value. In this specification, the image representing the change in luminance value between the tomographic images is referred to as an OCTA tomographic image, and the amount of change in luminance value is referred to as a motion contrast value (motion contrast data).

After an OCTA tomographic image is generated from tomographic images of a part of the subject to be inspected, three-dimensional OCTA volume data can be produced by generating an OCTA tomographic image in the same manner from tomographic images captured by successively changing the imaging position in the normal direction to the slices of the subject to be inspected. An image of the three-dimensional OCTA volume data projected in a direction perpendicular to the in-plane direction and the normal direction of the tomographic image is referred to as an OCTA image (OCTA front image).

Any method for calculating the motion contrast value involves a luminance value caused by random noise that occurs in the tomographic image. The change in luminance value caused by such noise is very significant, because the noise occurs randomly. Therefore, when an image representing the change in luminance value is generated, the change in luminance value caused by noise is visualized in a region where there is no object to be measured and the noise is dominant, so that the small change in luminance value in the blood vessel caused by movement of blood cells described above is less visible.

To overcome this problem, in Japanese Patent Application Laid-Open No. 2015-511146, there is described a method of omitting a motion contrast value caused by noise from values used for generation of a motion contrast image (OCTA image) by a threshold processing. According to Japanese Patent Application Laid-Open No. 2015-511146, a threshold $TH=B+2_o$ is set for the luminance value, where B denotes an average value of the background signals and $\sigma$ denotes a standard deviation of the background signals, and a luminance value greater than the threshold TH is regarded as a signal derived from the subject to be inspected, and a luminance value equal to or smaller than the threshold TH is regarded as noise. If the signal of a pixel is determined as noise, all the changes in luminance values of the pixels at the same coordinates as that pixel are determined as an invalid value, and the decorrelation value, which is the change in luminance value, is regarded as 0. In this way, the change in luminance value caused by noise is removed to render the small change in luminance value in the blood vessel described above.

However, according to the method based on the threshold processing disclosed in Japanese Patent Application Laid-Open No. 2015-511146, an OCTA image with low contrast may be generated in two cases described below.

In the first case, the threshold processing does not consider noise that occurs when the signal strength (luminance value) is high, so that the contrast of the OCTA image can be low. This occurs because the background signals are not the only noise, and there is noise in the measurement signals of the subject to be inspected.

In OCT, a detector detects interference light formed by reflection light from an object to be measured and light having passed through a reference light path. In general, when the detector detects light, the detector also detects noise referred to as optical shot noise that is proportional to the square root of the intensity of the light to be detected. The optical shot noise is considered as inevitable noise when the detector is used to detect light. Therefore, even when the intensity of the light detected is high, the optical shot noise always exists, and a change in signal strength (luminance value) caused by the optical shot noise occurs. The amount of the change in luminance value caused by the optical shot noise appears in the OCTA image as an insignificant motion contrast value. Therefore, because of the motion contrast value due to the optical shot noise, the OCT image may have a high luminance value at a location where no change in luminance value would otherwise occur, and as a result, the contrast of the OCTA image may decrease.

In the second case, the change in luminance value between the tomographic images occurs across the threshold. For example, when two tomographic images are used to calculate the change in luminance value (motion contrast value), one of the images may exhibit a signal strength greater than the threshold, whereas the other image exhibits a signal strength equal to or smaller than the threshold. In such a case, in the threshold processing described above, the motion contrast value, which is the calculation result of the change in luminance value, is regarded as 0 since one image exhibits a signal strength equal to or smaller than the threshold. However, at the relevant location, the other image exhibits a signal strength greater than the threshold, and this obviously shows that there is an object to be measured. Nevertheless, the calculated motion contrast value is regarded as being caused by noise, and the signal that would otherwise be regarded as indicating a change in luminance value in the blood vessel is removed. As a result, the motion contrast value decreases, and the contrast of the OCTA image decreases.

SUMMARY OF THE INVENTION

In view of such circumstances, the present invention provides an image processing apparatus, an optical coherence tomography apparatus, an image processing method and a computer readable medium that can generate a motion contrast image with higher contrast than an OCTA image generated based on the conventional threshold processing.

An image processing apparatus according to an implementation of the present invention comprises an acquisition unit that acquires a plurality of pieces of tomographic data indicating tomographic information on substantially a same part of a subject to be inspected, a threshold calculation unit that calculates a threshold from tomographic data associated with a target pixel for which motion contrast data is to be calculated, of the plurality of pieces of tomographic data, and a pixel value calculation unit that calculates a pixel value of the target pixel of a motion contrast image based on the threshold and the motion contrast data calculated from the tomographic data associated with the target pixel.

An image processing apparatus according to another implementation of the present invention comprises an acquisition unit that acquires a plurality of pieces of tomographic data indicating tomographic information on substantially a same part of a subject to be inspected and acquires a plurality of pieces of background data on an imaging optical system used for acquisition of the tomographic data on the subject to be inspected, a threshold calculation unit that calculates a background threshold $thn = N_{ave} + \beta \times N_\sigma$ from an average value $N_{ave}$ and a standard deviation $N_\sigma$ of the plurality of pieces of background data and a coefficient $\beta$, and a pixel value calculation unit that, based on the background threshold thn and tomographic data values $Ic_1$ and $Ic_2$ associated with a target pixel for which motion contrast data is to be calculated, sets a pixel value of the target pixel at 0 if a relation $Ic_1^2 + Ic_2^2 < thn^2$ is satisfied, and calculates the pixel value of the target pixel of a motion contrast image from the motion contrast data if the relation $Ic_1^2 + Ic_2^2 < thn^2$ is not satisfied.

Further features of the present invention will become apparent from the following description of exemplary embodiments with reference to the attached drawings.

BRIEF DESCRIPTION OF THE DRAWINGS

FIG. 14 shows a flow of an OCTA tomographic image generation processing according to the fourth exemplary embodiment.

DESCRIPTION OF THE EMBODIMENTS

Figure 1:
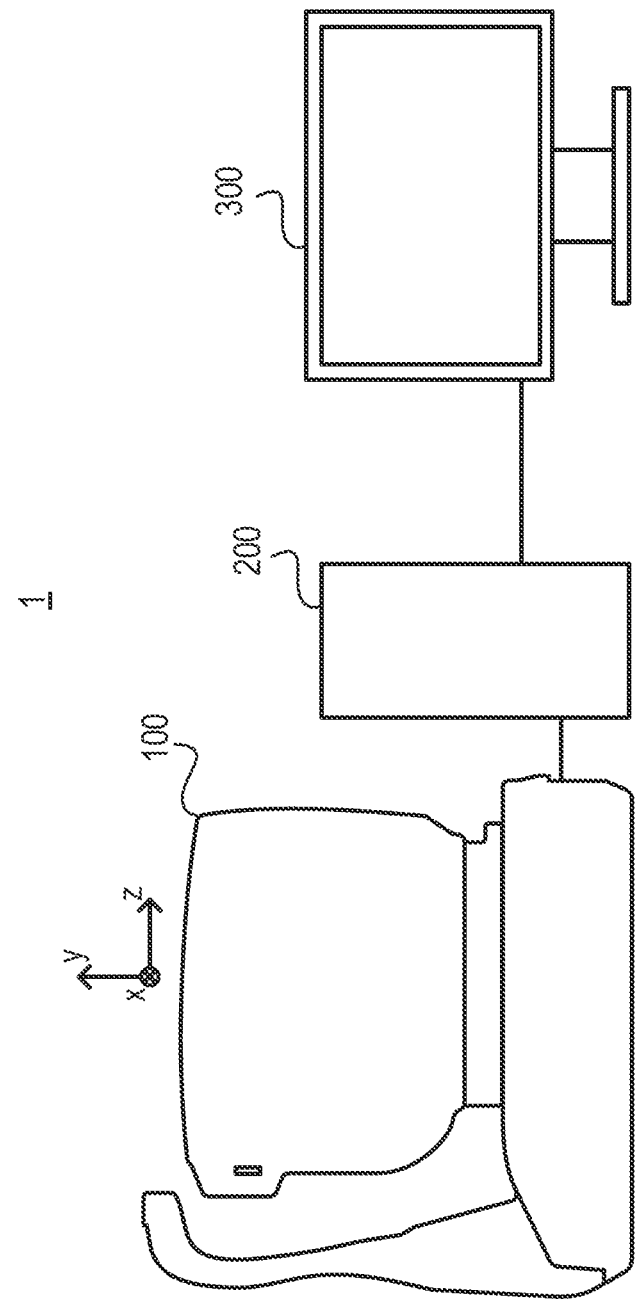
FIG. 1 shows a schematic configuration of an OCT apparatus according to a first exemplary embodiment of the present invention.

Preferred embodiments of the present invention will now be described in detail in accordance with the accompanying drawings.

Before describing exemplary embodiments of the present invention, an embodiment of the present invention will be schematically described below. In this embodiment, a new threshold processing is performed that addresses each of the cases described above in which an OCTA image with a low contrast is generated in the conventional threshold processing.

First, a threshold processing against optical shot noise will be described. In OCT, a light intensity of interference light formed by light on a measuring light path and light on a reference light path is acquired as an interference signal. Therefore, when the light intensity is acquired, inevitable optical shot noise is acquired at the same time. In OCT, after the interference signal is acquired, the interference signal is Fourier-transformed on the optical frequency axis to acquire tomographic information on a subject to be inspected. If the tomographic information is acquired based on the interference signal containing optical shot noise, the signal strength in the tomographic information contains a fluctuation due to the optical shot noise.

The fluctuation in signal strength due to the optical shot noise occurs even if the subject to be inspected or the measurement apparatus (interferometer) is not moving. Therefore, if data containing a fluctuation in signal strength due to optical shot noise is used to generate an OCTA image, the generated OCTA image may include a pixel value based on a change in luminance value at a location where no change in luminance value would otherwise occur. This means that the OCTA image contains noise information, and the contrast (contrast to noise ratio) of the OCTA image is low.

It is generally known that, supposing that the light intensity is denoted by Li, the optical shot noise is expressed as $Li/\sqrt{Li}$ in terms of signal to noise ratio (SNR). If the change in luminance value in a tomographic image falls within a range of $\sqrt{S}$ with respect to the luminance value S of the tomographic image, it cannot be determined whether the change in luminance value is a change in luminance value due to the optical shot noise or a change in luminance value due to a relevant change of the subject to be inspected.

In this embodiment, a change in luminance value equal to or smaller than $\sqrt{S}$ with respect to the luminance value S of the tomographic image is not used to generate an OCTA image. That is, a threshold for a change in luminance value used to generate an OCTA image is set based on $\sqrt{S}$. Since $\sqrt{S}$ is a standard deviation $\sigma$ of the optical shot noise, a change in luminance falling within a range several times greater than the standard deviation a may be removed in order to remove noise with higher reliability.

Next, a threshold processing against noise (background noise) of the measurement apparatus (interferometer) across the threshold will be described. The background noise can be acquired by performing measurement without any subject to be inspected placed and detecting an optical signal without any return light from the subject to be inspected. The background signal can be Fourier-transformed to generate a background signal in the dimensions of the tomographic image. The background signal includes a significant fluctuation in signal strength due to the noise, and a signal having a magnitude several times greater than the standard deviation $\sigma$ of the background signal with respect to an average value of the background signal can be background noise. Therefore, a value several times greater than the standard deviation $\sigma$ of the background signal can be used as a threshold. Alternatively, the background signal may be acquired by inserting a light shield in an optical system for detecting the measuring light to block the measuring light.

When an OCTA image is generated, a change in luminance value between two pixels at the same coordinates (pixel locations) in two aligned tomographic images is calculated. In the conventional threshold processing method, if the luminance value (pixel value) of one of the tomographic images is smaller than the threshold, the change in luminance value at the coordinates is not used to generate the OCTA image.

However, the luminance value at the coordinates in the other tomographic image may be significantly greater than the threshold. The luminance value of such a pixel is considered as a significant signal. Therefore, it can be considered that the luminance value of the one tomographic image is smaller than the threshold because the significant signal strength has fluctuated due to movement of the subject to be inspected and decreased to approximately the strength of the background signal of the measurement apparatus. Therefore, the change in luminance value at such a pixel should be used to generate the OCTA image, and the pixel should be regarded as a pixel that properly represents the movement of the subject to be inspected.

In view of this, in this embodiment, when the change in luminance value is calculated from two tomographic images, even if the luminance value at a pixel in one tomographic image is not greater than a predetermined threshold, the change in luminance value at the pixel is used to generate the OCTA image if the luminance value at the corresponding pixel in the other tomographic image is greater than the threshold. This embodiment proposes a new threshold processing that can provide such a processing result.

In the proposed new threshold processing, the background noise distribution is considered. The background noise distribution is basically the same in any tomographic image as far as the measurement is performed with the same apparatus in the same environment. Considering that the background noise distribution is a normal distribution, a probability distribution P(I) of the background noise with respect to the luminance value I is expressed by the following formula using an arbitrary coefficient c.

$$P(I) \propto e^{-cI^2}$$

A probability distribution $P(I_1, I_2)$ of the probability that luminance values $I_1$ and $I_2$ at pixels at the same coordinates (pixel locations) in two tomographic images are noises can be expressed by the following formula, since the tomographic image data are independent from each other.

$$P(I_1, I_2) = P(I_1) P(I_2)$$

$$P(I_1)P(I_2) \propto e^{-cI_1^2} e^{-cI_2^2} = e^{-c(I_1^2+I_2^2)} = e^{-cr^2}$$

Therefore, it can be considered that the conventionally known shape of the background noise distribution of each of the two tomographic images and the shape of the background noise distribution of the two tomographic images in the direction of the radius (r) from the origin of a coordinate system whose axes indicate the luminance values $I_1$ and $I_2$ are the same. Therefore, in order to remove the background noise, a threshold can be set along an arc centered on the origin. The threshold can be a value represented by a sum of an average value of the luminance value I and the standard deviation $\sigma$ increased several times that is determined so that most of the background noise described above lies within the arc with the radius r.

According to this embodiment, by such a threshold processing, a value of a change in luminance due to a movement of a blood cell, which would be removed in the conventional threshold processing, can be used to generate an OCTA image, and an OCTA image with high contrast can be generated.

In the following, exemplary embodiments of the present invention will be described in detail with reference to the drawings. The dimensions, materials, shapes and relative positions of components described in the exemplary embodiments below are arbitrary and can be modified according to the particular configuration of the apparatus to which the present invention is applied or various conditions. Throughout the drawings, the same reference numerals are used to denote the same elements or elements having similar functions.

First Exemplary Embodiment

In the following, with reference to FIGS. 1 to 6D, an optical coherence tomography apparatus (OCT apparatus) and an image processing method according to a first exemplary embodiment of the present invention will be described. FIG. 1 shows a schematic configuration of an OCT apparatus 1 according to this exemplary embodiment. The OCT apparatus 1 includes an imaging optical system 100, a control unit 200 (image processing apparatus), and a display unit 300.

The imaging optical system 100 illuminates an eye to be inspected, which is a subject to be inspected, with measuring light, detects interference light formed by return light from the eye to be inspected and reference light, and generates an interference signal. The control unit 200 is connected to the imaging optical system 100 and the display unit 300 and controls the imaging optical system 100 and the display unit 300. The control unit 200 can acquire the interference signal generated by the imaging optical system 100 and generate a tomographic image of the eye to be inspected. The display unit 300 can display various images and information on the eye to be inspected transmitted from the control unit 200.

The control unit 200 may be a general-purpose computer or a dedicated computer for the imaging optical system 100. The display unit 300 may be any display. Although the imaging optical system 100, the control unit 200 and the display unit 300 are shown as separate components in this exemplary embodiment, all or part of these components may be integrated with each other.

(Configuration of Imaging Optical System)

Figure 2:
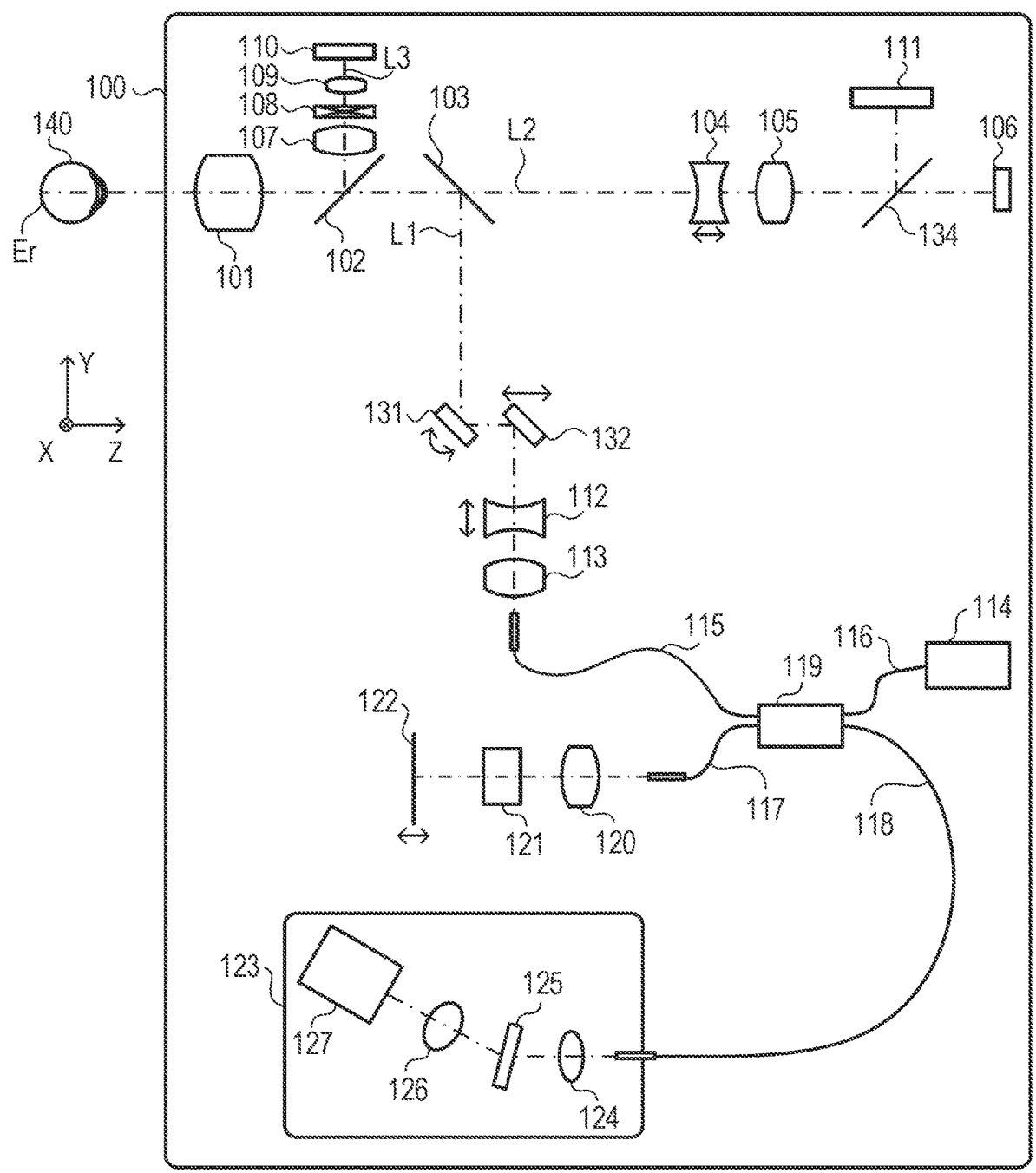
FIG. 2 shows a schematic configuration of an imaging optical system according to the first exemplary embodiment.

Next, with reference to FIG. 2, a configuration of the imaging optical system 100 according to this exemplary embodiment will be described. FIG. 2 shows a schematic configuration of the imaging optical system 100.

In the imaging optical system 100, an objective lens 101 is arranged to face an eye to be inspected 140. A dichroic mirror 102 and a dichroic mirror 103 are arranged on an optical axis of the objective lens 101. The optical path from the objective lens 101 is branched by the dichroic mirrors 102 and 103 into an optical path L1 of an OCT optical system, an optical path L2 for an internal fixation lamp and a fundus observation system, and an optical path L3 for an anterior eye portion observation system according to the wavelength band of the light on the optical path. In this exemplary embodiment, the optical path L1 for the OCT optical system and the optical path L2 for the internal fixation lamp and the fundus observation system are arranged in the direction of transmission of the dichroic mirror 102, and the optical path L3 for the anterior eye portion observation system is arranged in the direction of reflection of the dichroic mirror 102. The optical path L2 for the internal fixation lamp and the fundus observation system is arranged in the direction of transmission of the dichroic mirror 103, and the optical path L1 for the OCT optical system is arranged in the direction of reflection of the dichroic mirror 103. However, the arrangement of the optical paths is not limited to the arrangement described above, and the optical paths arranged in the directions of transmission of the dichroic mirrors 102 and 103 may be arranged in the directions of reflection of the dichroic mirrors 102 and 103, and vice versa.

On the optical path L2, lenses 104 and 105, a dichroic mirror 134, an internal fixation lamp 106, and a fundus observation CCD 111 are arranged. The components arranged on the optical path for the fundus observation system form a fundus observation optical system. The lens 104 is a focusing lens and is driven by a motor (not shown) controlled by the control unit 200 in the optical axis direction indicated by an arrow in the drawing in order to adjust focusing of the light on the optical path L2. The optical path L2 is branched by the dichroic mirror 134 into an optical path leading to the internal fixation lamp 106 and an optical path leading to the CCD 111. In this exemplary embodiment, the internal fixation lamp 106 is arranged in the direction of transmission of the dichroic mirror 134, and the CCD 111 is arranged in the direction of reflection of the dichroic mirror 134. Alternatively, the CCD 111 may be arranged in the direction of transmission of the dichroic mirror 134, and the internal fixation lamp 106 may be arranged in the direction of reflection of the dichroic mirror 134.

The CCD 111 is sensitive to a wavelength of fundus observation illumination light (not shown), specifically, a wavelength of about 780 nm. The internal fixation lamp 106 emits visible light and is used to facilitate vision fixation of a subject.

The return light, which is light emitted by the fundus observation light source and is reflected by the eye to be inspected 140, passes through the objective lens 101 and the dichroic mirrors 102 and 103 to enter the optical path L2. The return light having entered the optical path L2 passes through the lenses 104 and 105 and is reflected by the dichroic mirror 134 and guided to the CCD 111. The CCD 111 detects the incident return light from the eye to be inspected 140 and generates a signal corresponding to the return light. The control unit 200 can acquire a front image of a fundus Er of the eye to be inspected 140 based on the signal generated by the CCD 111.

The light emitted by the internal fixation lamp 106 passes through the dichroic mirror 134, the lenses 104 and 105, the dichroic mirrors 103 and 102 and the objective lens 101 and then incident on the eye to be inspected 140. The internal fixation lamp 106 can provide light of any shape at any location on the eye to be inspected 140 as a vision fixation target to facilitate vision fixation of the subject.

The configuration of the fundus observation optical system is not limited to the configuration described above and may be a configuration of a scanning laser ophthalmoscope (SLO) that scans the eye to be inspected with illumination light, for example. In that case, light of any shape can be provided as a vision fixation target at any location on the eye to be inspected 140 to facilitate vision fixation of the subject by making the internal fixation lamp 106 blink in synchronization with the movement of the scanning unit of the SLO optical system.

Next, the optical path L3 for the anterior eye portion observation system will be described. On the optical path L3 for the anterior eye portion observation system, lenses 107 and 109, a split prism 108, and an anterior eye portion observation CCD 110 that detects infrared light are arranged. The components arranged on the optical path L3 for the anterior eye portion observation system form an anterior eye portion observation optical system.

On the optical path L3, a light source (not shown) irradiates an anterior eye portion of the eye to be inspected 140 with anterior eye portion observation light having a wavelength of about 970 nm. A reflection light from the anterior eye portion of the eye to be inspected 140 is incident on the split prism 108 via the objective lens 101, the dichroic mirror 102 and the lens 107. The split prism 108 is arranged at a location conjugate with a pupil of the eye to be inspected 140. The light exiting the split prism 108 is incident on the CCD 110 via the lens 109.

The CCD 110 is designed to detect light having a wavelength of about 970 nm, and detects the reflection light from the anterior eye portion and generates a signal corresponding to the reflection light from the anterior eye portion. The control unit 200 can generate an image of the anterior eye portion of the eye to be inspected 140 based on the signal generated by the CCD 110. In this process, since the CCD 110 detects the reflection light having passed through the split prism 108, the control unit 200 can determine, from a split image of the anterior eye portion, the distance between the eye to be inspected 140 and the imaging optical system 100 in the Z direction (depth direction).

Next, the optical path L1 will be described. The optical path L1 forms the optical path for the OCT optical system as described above, and is used to acquire an interference signal for generation of a tomographic image of the eye to be inspected 140. On the optical path L1, an X scanner 131, a Y scanner 132, and lenses 112 and 113 are arranged.

The X scanner 131 and the Y scanner 132 form a scanning unit that scans the fundus Er of the eye to be inspected 140 with the measuring light. The X scanner 131 and the Y scanner 132 are driven by a galvano-motor (not shown) controlled by the control unit 200. The X scanner 131 is used to scan the fundus with the measuring light in the X direction, and the Y scanner 132 is used to scan the fundus with the measuring light in the Y direction. The X scanner 131 and the Y scanner 132 can be constituted by any deflection mirror, such as a galvano-mirror. Although the scanning unit is formed by the X scanner 131 and the Y scanner 132 in this exemplary embodiment, the configuration of the scanning unit is not limited to this configuration. The scanning unit may be constituted by a single deflection mirror, such as an MEMS mirror, that can two-dimensionally deflect light by itself.

The lens 112 is a focusing lens used to adjust focusing of the measuring light emitted from an optical fiber 115 of an OCT measurement optical system to the fundus Er of the eye to be inspected 140. The lens 112 is driven by a motor (not shown) controlled by the control unit 200 in the optical axis direction of the measuring light shown by an arrow in the drawing. The focusing adjustment also allows the return light from the fundus Er to be focused as a spot and incident on a tip end of the optical fiber 115. The optical fiber 115, the optical members arranged on the optical path L1, the dichroic mirrors 102 and 103 and the objective lens 101 form the OCT measurement optical system in which the measuring light propagates in the OCT optical system.

The optical fiber 115 is connected to an optical coupler 119. To the optical coupler 119, an optical fiber 115 of an OCT measurement optical system, an optical fiber 116 connected to a light source 114, an optical fiber 117 of an OCT reference optical system, and an optical fiber 118 connected to a spectroscope 123 are connected. The optical coupler 119 serves as a splitter that splits the light from the light source 114 into the measuring light and the reference light and an interference unit that makes the return light of the measuring light from the eye to be inspected 140 and the reference light interfere with each other to produce interference light.

The light source 114 is a super luminescent diode (SLD), which is a typical low-coherence light source. In this exemplary embodiment, the light source 114 emits light having a central wavelength of 855 nm and a wavelength bandwidth of about 100 nm. However, the configuration of the light source 114 is not limited to this configuration, and any light source can be used depending on the desired configuration.

The light emitted from the light source 114 passes through the optical fiber 116 and is split by the optical coupler 119 into the measuring light that is to propagate through the OCT measurement optical system such as the optical fiber 115 and the reference light that is to propagate through the OCT reference optical system such as the optical fiber 117. The measuring light passes through the optical path L1 for the OCT optical system described above and is applied to the fundus Er of the eye to be inspected 140, which is an observation target, and reflected or scattered by the retina of the eye to be inspected 140, and the return light passes through the same optical path and reaches the optical coupler 119.

On the other hand, the reference light reaches a reference mirror 122 through the optical fiber 117, the lens 120 and a dispersion compensating glass 121, which is inserted to make the dispersions of the measuring light and the reference light agree with each other, and is reflected by the reference mirror 122. The light then passes through the same optical path and reaches the optical coupler 119. The optical fiber 117, the lens 120, the dispersion compensating glass 121 and the reference mirror 122 form the OCT reference optical system.

The return light of the measuring light from the eye to be inspected 140 and the reference light are combined by the optical coupler 119 into interference light. The return light of the measuring light and the reference light interfere with each other to form interference light when the optical path length of the measuring light and the optical path length of the reference light are substantially equal to each other. The reference mirror 122 is held by a motor and a driving mechanism (both not shown) controlled by the control unit 200 in such a manner that the reference mirror 122 can be adjusted in the optical axis direction of the reference light indicated by an arrow in the drawing, so that the optical path length of the reference light can be adjusted to the optical path length of the measuring light, which changes depending on the measured part of the eye to be inspected 140. The interference light is guided to the spectroscope 123 through the optical fiber 118.

In the spectroscope 123 (light detection unit), lenses 124 and 126, a diffraction grating 125 and a line sensor 127 are provided. The interference light exiting the optical fiber 118 is shaped by the lens 124 into substantially parallel light, dispersed by the diffraction grating 125, and then focused on the line sensor 127 by the lens 126. The line sensor 127 is shown as an example of a light receiving element that receives the interference light and generates and outputs an interference signal corresponding to the interference light. Based on the signal generated by the line sensor 127, the control unit 200 can acquire information on slices of the fundus Er of the eye to be inspected 140 and generate a tomographic image of the fundus Er.

(Configuration of Control Unit 200)

Figure 3:
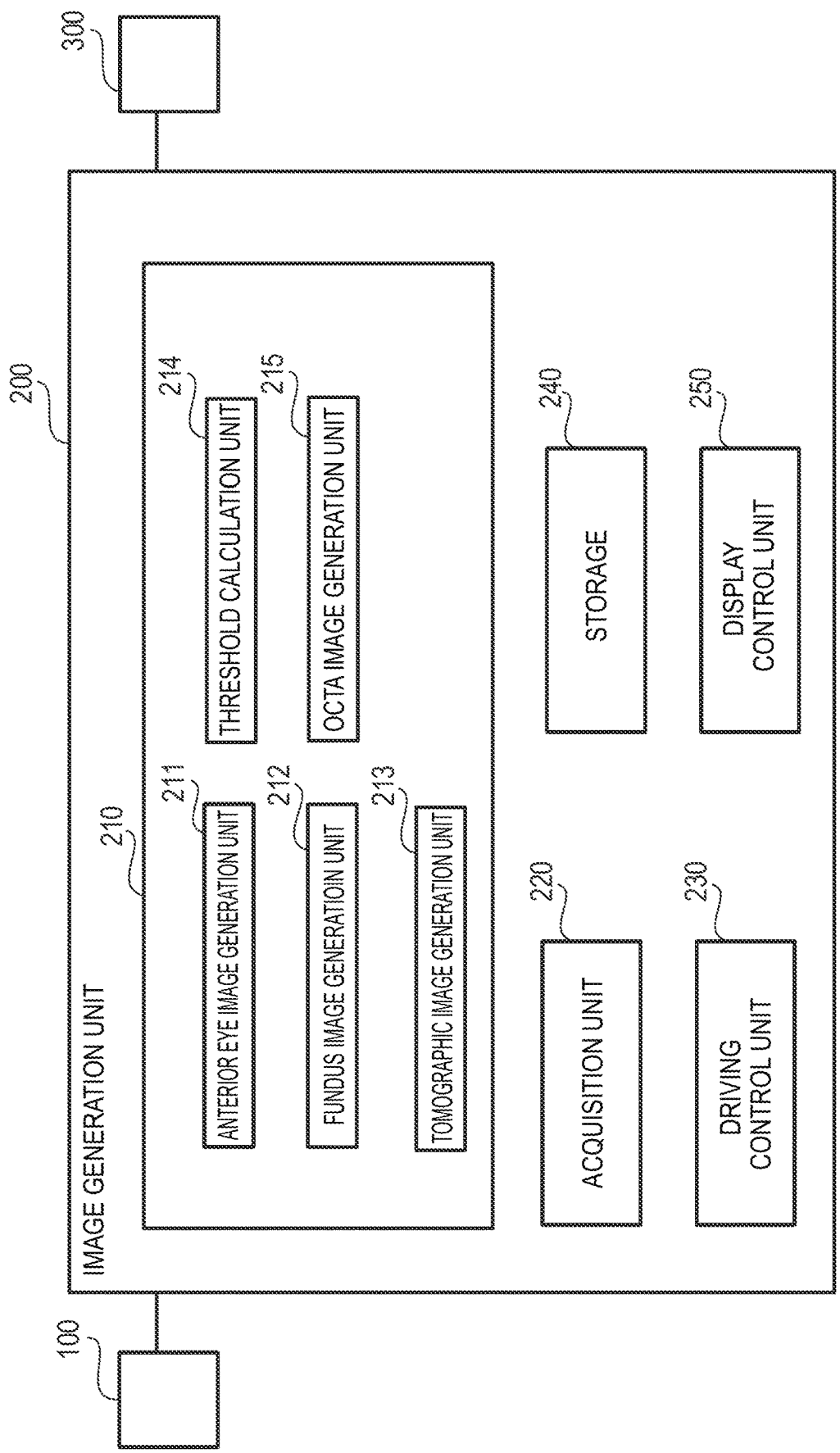
FIG. 3 shows a schematic configuration of a control unit according to the first exemplary embodiment.

With reference to FIG. 3, a configuration of the control unit 200 will be described. FIG. 3 is a block diagram showing a schematic configuration of the control unit 200.

The control unit 200 includes an image generation unit 210, an acquisition unit 220, a driving control unit 230, a storage 240, and a display control unit 250.

The acquisition unit 220 acquires various signals from the CCDs 110 and 111 of the imaging optical system 100 and the line sensor 127. The acquisition unit 220 can also acquire a Fourier-transformed signal generated based on the interference signal or this signal further subjected to some signal processing, for example, from the tomographic image generation unit 213.

The image generation unit 210 includes an anterior eye image generation unit 211, a fundus image generation unit 212, the tomographic image generation unit 213, a threshold calculation unit 214, and an OCTA image generation unit 215 (pixel value calculation unit).

The anterior eye image generation unit 211 generates an anterior eye image of the eye to be inspected 140 based on the signal from the CCD 110 acquired by the acquisition unit 220. The fundus image generation unit 212 generates a fundus image of the eye to be inspected 140 based on the signal from the CCD 111 acquired by the acquisition unit 220.

The tomographic image generation unit 213 generates a tomographic image of the eye to be inspected 140 based on the interference signal from the line sensor 127 acquired by the acquisition unit 220. More specifically, the tomographic image generation unit 213 Fourier-transforms the interference signal acquired from the line sensor 127 through the series of processes described above, and converts the Fourier-transformed signal into luminance or density information. The tomographic image generation unit 213 thereby generates a tomographic image of the fundus Er of the eye to be inspected 140 in the depth direction (Z direction) at a certain point. Such a scanning scheme is referred to as an A-scan, and the acquired tomographic image is referred to as an A-scan image.

A plurality of A-scan images can be acquired by repeatedly performing such A-scan while the X scanner 131 and the Y scanner 132 scanning the fundus Er with the measuring light in a predetermined transverse direction. For example, if the fundus Er is scanned with the measuring light in the X direction by the X scanner 131, a tomographic image in the XZ plane is acquired, and if the fundus Er is scanned with the measuring light in the Y direction by the Y scanner 132, a tomographic image in the YZ plane is acquired. The scheme of scanning the fundus Er of the eye to be inspected 140 in a predetermined transverse direction in this way is referred to as a B-scan, and the acquired tomographic image is referred to as a B-scan image.

The threshold calculation unit 214 calculates a threshold used for generation of an OCTA image based on tomographic data such as the interference signal from the line sensor 127 acquired by the acquisition unit 220. The tomographic data may include one of the interference signal, the Fourier-transformed signal generated based on the interference signal, the latter signal further subjected to some signal processing, and the tomographic image generated by the tomographic image generation unit 213.

The OCTA image generation unit 215 calculates motion contrast data on the eye to be inspected 140 using the tomographic data acquired by the acquisition unit 220 and the threshold calculated by the threshold calculation unit 214, and generates an OCTA image based on the motion contrast data.

In this exemplary embodiment, an arrangement in which the OCTA image generation unit 215 calculates the motion contrast data based on the change in luminance value of the tomographic image will be described. However, the method of calculating the motion contrast data is not limited to this. For example, the motion contrast data may be obtained by using Fourier-transformed complex OCT signals (interference signals) and calculating the difference in strength between the complex OCT signals. In that case, the OCTA image generation unit 215 can determine the final motion contrast data as one of an average value and a maximum value of the strength differences. The OCTA image generation unit 215 may adopt a known method of calculating the motion contrast data using strength information (luminance information) on the Fourier-transformed complex OCT signals.

The driving control unit 230 controls driving of the components of the imaging optical system 100 such as the light source 114, the X scanner 131 and the Y scanner 132. The storage 240 stores various images generated by the image generation unit 210, input information on the subject, or a program constituting the control unit 200, for example. The display control unit 250 controls the display unit 300 and makes the display unit 300 display the various images, the information on the subject or the like stored in the storage 240.

Each component of the control unit 200 can be constituted by a module executed by a CPU or MPU of the control unit 200. Alternatively, each component of the control unit 200 may be constituted by a circuit or the like such as ASIC that performs a particular function. The storage 240 can be constituted by any storage medium such as a memory or an optical disk.

(Imaging Processing for Tomographic Image)

Figure 4A:
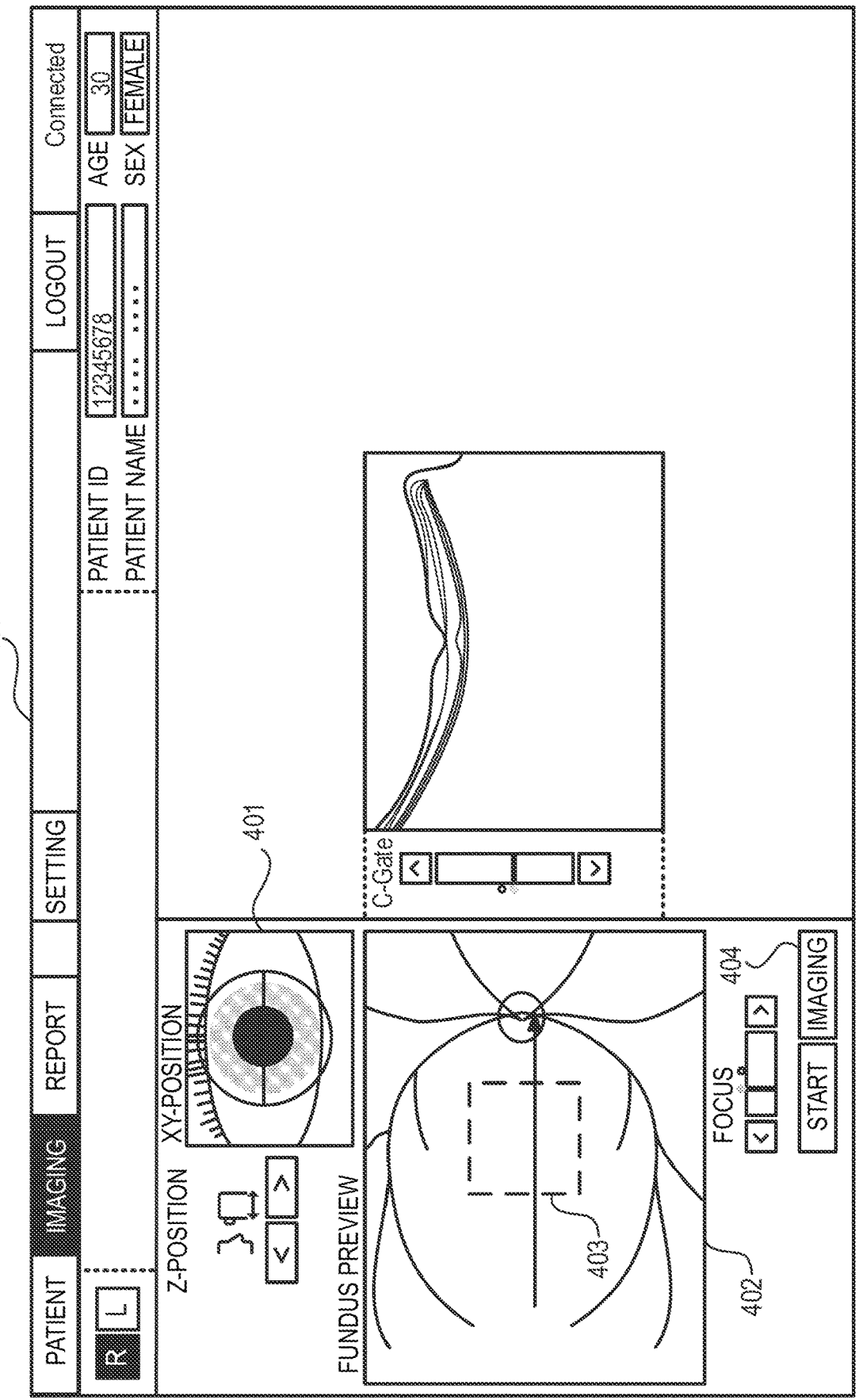
FIG. 4A shows an example of a preview window according to the first exemplary embodiment.
Figure 4B:
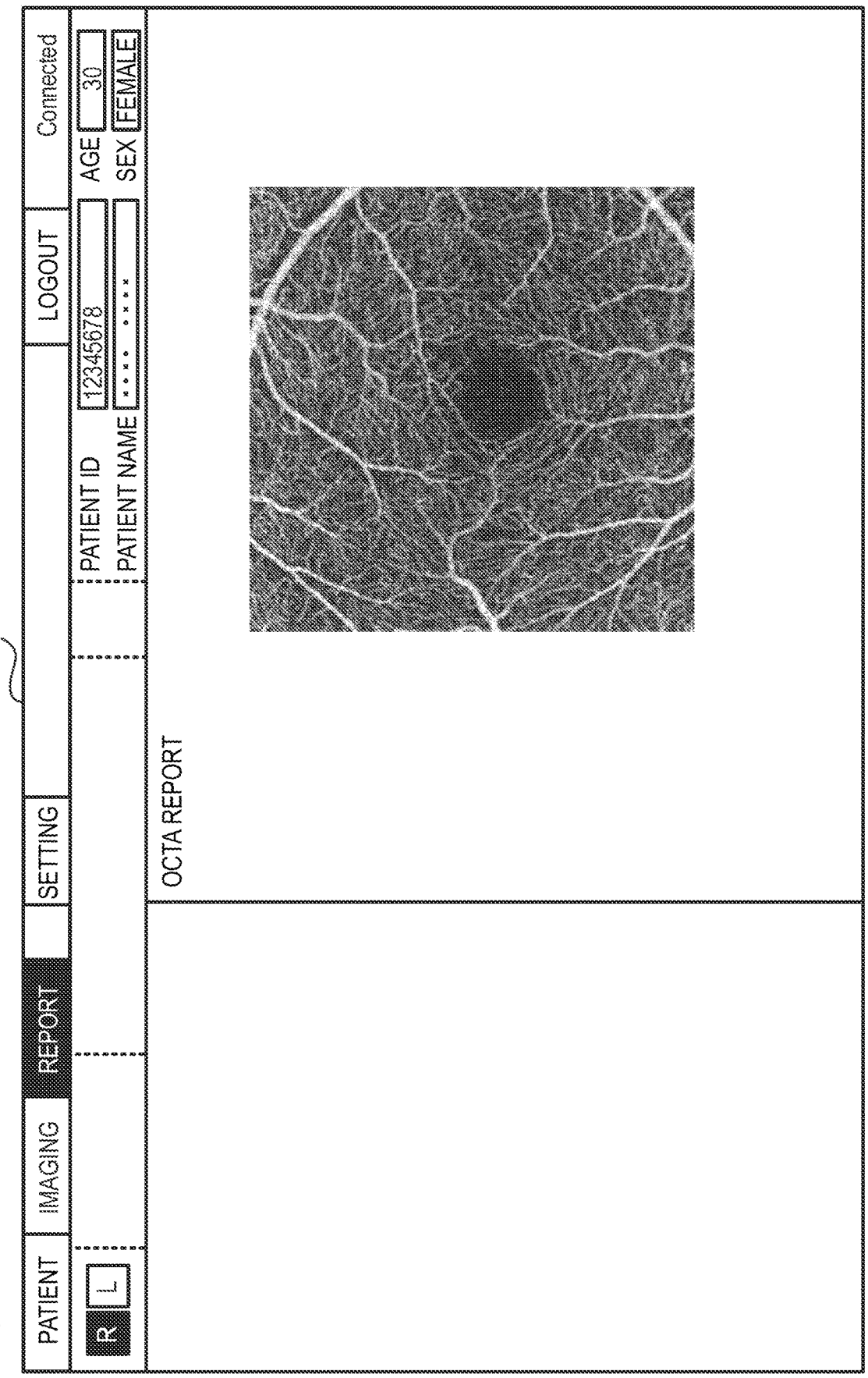
FIG. 4B shows an example of a report window according to the first exemplary embodiment.

In the following, with reference to FIGS. 4A to 6D, an imaging processing for a tomographic image according to this exemplary embodiment will be described. FIG. 4A shows an example of a preview window 400 of a control/image display GUI displayed on the display unit 300. FIG. 4B shows an example of a report window 405 of the control/image display GUI displayed on the display unit 300. The preview window 400 shown in FIG. 4A is a window displayed for performing instruction to start imaging, alignment adjustment of the imaging optical system 100, and adjustment of the position of the part to be imaged, for example. On the other hand, the report window 405 shown in FIG. 4B is a window for displaying the OCTA image generated in the imaging processing. Although not described in this exemplary embodiment, the display unit 300 may display a report window for displaying the generated tomographic image or OCTA tomographic image, for example.

In this exemplary embodiment, after preparations for the imaging are made in the preview window 400 shown in FIG. 4A, the OCT apparatus 1 is used to image the fundus Er of the subject. More specifically, first, the face of the subject is placed on a face rest of the imaging optical system 100, and alignment of the imaging optical system 100 with respect to the eye to be inspected 140 is performed so that the measuring light is incident on the pupil of the eye to be inspected 140. In this exemplary embodiment, an examiner performs the alignment of the imaging optical system 100 by moving the imaging optical system 100 in the X, Y and Z directions with a driving stage (not shown) while checking an anterior eye image 401 on the preview window 400 or a fundus image 402 displayed in a fundus preview. As described above, the anterior eye image 401 is generated by the anterior eye image generation unit 211, and the fundus image 402 is generated by the fundus image generation unit 212. Alternatively, the control unit 200 may perform the alignment of the imaging optical system 100 with respect to the eye to be inspected 140 by analyzing the anterior eye image 401 and other images and controlling driving of the imaging optical system 100 based on the result of the analysis.

The examiner then sets an imaging range 403 for the OCTA image with an input unit (not shown), such as a mouse, and then starts imaging by clicking an imaging button 404 or pressing an imaging button associated with the imaging optical system 100. The imaging range 403 may be set with respect to a part to be measured by inputting the part to be measured of the eye to be inspected 140 and analyzing the fundus image 402 or the like. Alternatively, the imaging may be started when a predetermined time has lapsed after setting of the imaging range 403.

(Processing Flow of Tomographic Image)

Figure 5A:
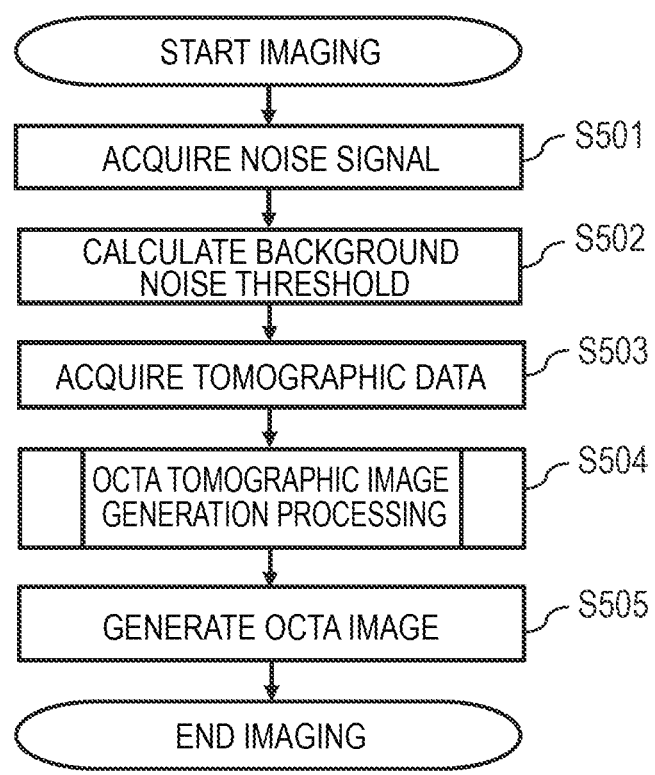
FIG. 5A shows a flow of an imaging processing according to the first exemplary embodiment.
Figure 5B:
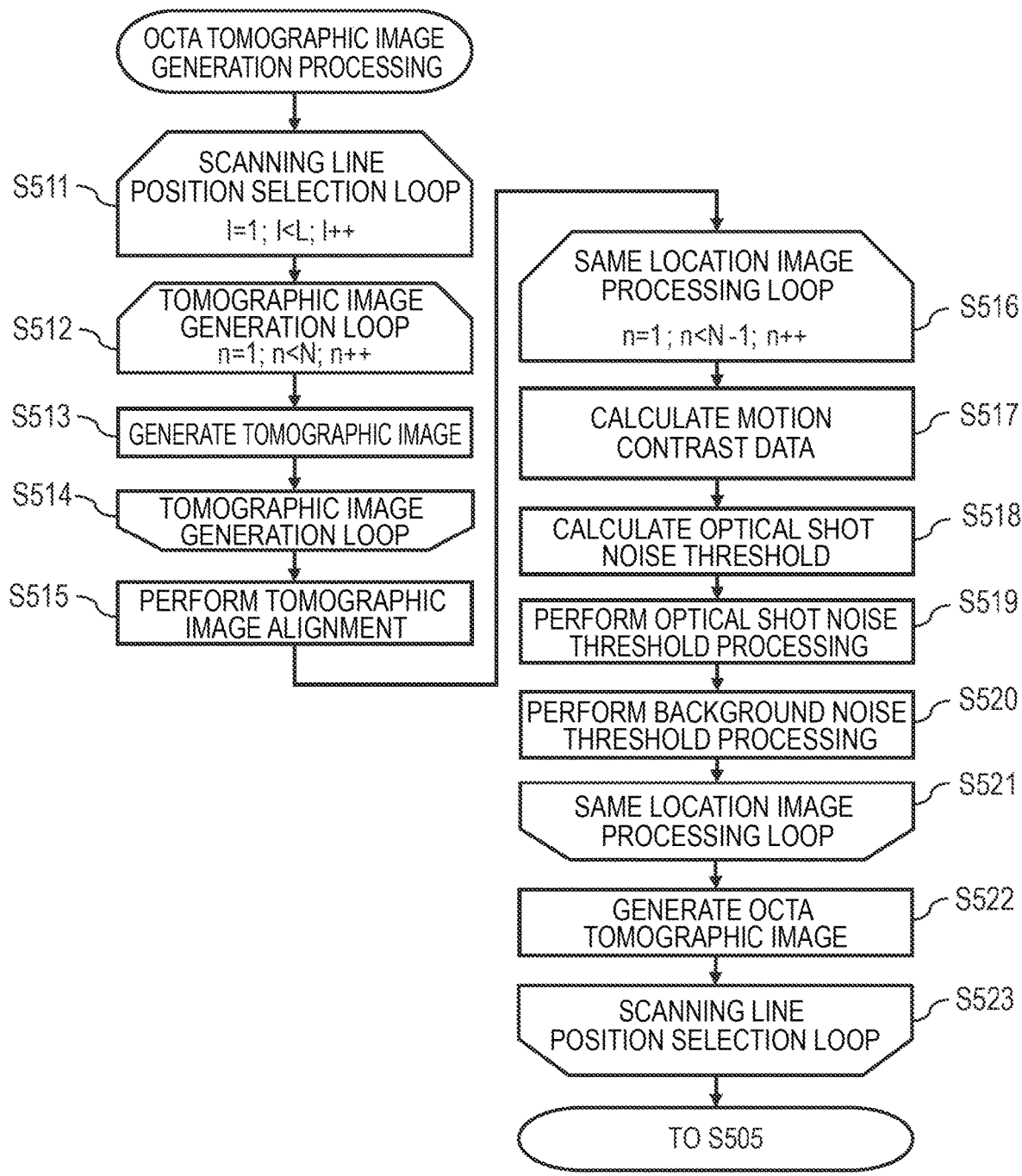
FIG. 5B shows a flow of an OCTA tomographic image generation processing according to the first exemplary embodiment.

FIG. 5A is a flowchart showing a process of capturing and processing a tomographic image according to this exemplary embodiment, and FIG. 5B is a flowchart showing an OCTA tomographic image generation processing. When imaging is started, the process proceeds to Step S501.

In Step S501, the tomographic image generation unit 213 acquires a background signal (background data) plural times as a noise signal of the OCT optical system. The number of times of acquisition of the background signal can be any number and M in this exemplary embodiment. The background signal is acquired by acquiring an optical signal constituted only by the reference signal by blocking the return light of the measuring light, for example. The tomographic image generation unit 213 may acquire a noise signal such as a background signal measured for each apparatus in advance and stored in the storage 240.

In Step S502, first, the tomographic image generation unit 213 generates a background image using the M noise signals acquired in Step S501. Then, the threshold calculation unit 214 calculates a background noise threshold thn (background threshold thn) using the generated M background images.

More specifically, the threshold calculation unit 214 calculates an average value $N_{ave}$ and a standard deviation $N_\sigma$ of the luminance values of the generated M background images. The threshold calculation unit 214 then calculates a sum of the average value $N_{av}$ and the standard deviation $N_\sigma$ multiplied by a positive coefficient β, $N_{ave}+β×N_\sigma$, as the background noise threshold thn. A common background noise threshold thn may be calculated for all the pixels, or a background noise threshold thn may be calculated for each pixel location in the depth direction. In the latter case, the average value $N_{ave}$ and the standard deviation $N_\sigma$ can be calculated for each pixel location in the depth direction of the M background images, and the sum $N_{ave}+β×N_\sigma$ for each pixel location can be used as the background noise threshold for each pixel location. When acquiring the background signal, the background signal (background data) may be acquired plural times at each scan location at which the measurement signal is acquired, and the background noise threshold thn may be calculated for each scan location corresponding to each pixel location.

The threshold calculation unit 214 stores the calculated background noise threshold thn in the storage 240. The background noise threshold may be stored in the storage 240 in advance.

The coefficient β can be any value and is 7 (β=7) in this exemplary embodiment. As the coefficient β increases, the probability that the luminance value greater than the background noise threshold thn is derived from the subject to be inspected increases. However, if the coefficient β is too great, a luminance value derived from the subject to be inspected can be determined as noise. For example, the coefficient β can be adjusted while observing the final OCTA image subjected to the threshold processing described later.

In Step S503, the imaging optical system 100 images the fundus Er of the eye to be inspected 140, and the acquisition unit 220 acquires the interference signal for the fundus Er as tomographic data. More specifically, first, the driving control unit 230 controls the components of the imaging optical system 100 to perform B-scans N times on substantially the same part (along the scanning line) of the eye to be inspected 140 in the X and Z directions to achieve optical coherence tomography of the fundus Er. In this way, the acquisition unit 220 acquires N sets of interference signals obtained by N B-scans. Although N=3 is adopted and the optical coherence tomographic imaging is performed three times in this exemplary embodiment, the number of times of imaging is not limited to three. The number N of times of imaging, which is the number of tomographic images used for calculating the change in luminance used for generating the OCTA image, can be any value equal to or greater than 2. In the following description, a group of interference signals associated with one B-scan will be referred to as a set of interference signals. Similarly, a group of tomographic signals associated with one B-scan will be referred to as a set of tomographic signals. The phrase "substantially the same part" does not mean only exactly the same part but includes a part slightly different from the relevant part.

The driving control unit 230 then controls the components of the imaging optical system 100 to displace the scanning line by a predetermined distance in the Y direction and perform B-scans N times again, and the acquisition unit 220 acquires N sets of interference signals from the imaging optical system 100. The driving control unit 230 repeats the imaging processing to achieve scanning of L parts. In this way, the acquisition unit 220 acquires L×N sets of interference signals. In the following, an n-th set of interference signals for an l-th scanning line will be denoted as $In_{(l, n)}$. The luminance value and other values will also be denoted by similar subscripts. Although L=232 is adopted and the measurement part is displaced 231 times in the Y direction in this exemplary embodiment, L is not limited to 232 and can be arbitrarily set depending on the desired configuration. Furthermore, although the measurement part is displaced by 13 μm each time the measurement is made, the distance can be arbitrarily set depending on the desired configuration. For example, the eye to be inspected 140 can be imaged with higher density if the distance of the displacement of the measurement part is reduced, and L is increased.

After the L×N sets of interference signals are acquired in Step S503, the control unit 200 proceeds to Step S504. In Step S504, the tomographic image generation unit 213 generates a tomographic image using the L×N sets of interference signals, and the OCTA image generation unit 215 generates an OCTA tomographic image. In the following, with reference to FIG. 5B, a process flow of Step S504 will be described.

Once the process of Step S504 is started, in Step S511, the image generation unit 210 selects the position of the scanning line at which the interference signals used to generate the tomographic image and the OCTA tomographic image are acquired. In Step S511, the image generation unit 210 first selects the scanning line (the scanning line position l=1). The image generation unit 210 then proceeds to Step S512. After the process from Step S512 to Step S522 is ended, the image generation unit 210 compares l with L. If 1 is smaller than L, the image generation unit 210 increments 1 by 1 and repeats the process from Step S512 to Step S522.

In Step S512, the image generation unit 210 selects a set of interference signals used for generating a tomographic image. Since N sets of interference signals are acquired for each scanning line as described above, the image generation unit 210 selects the n-th set of interference signals for the scanning line position l. In Step S512, the image generation unit 210 first selects the set (n=1) of interference signals In(l, 1). The image generation unit 210 then proceeds to Step S513. After the processing of Step S513 is ended, the image generation unit 210 compares n with N. If n is smaller than N, the image generation unit 210 increments n by 1 and repeats the processing of Step S513.

In Step S513, the tomographic image generation unit 213 generates a tomographic image from the interference signals $In_{(l,\ n)}$ selected by the image generation unit 210. More specifically, the tomographic image generation unit 213 performs a one-dimensional Fourier transformation on the interference signal at each A-scan location of the interference signals $In_{(l,\ n)}$ to calculate the amplitude of the calculated signal. The amplitude is the luminance value of each pixel of the tomographic image corresponding to one A-scan. The tomographic image generation unit 213 generates a tomographic image $C_{(l,\ n)}$ by performing this processing for the interference signals for one B-scan. This exemplary embodiment has been described as performing only the Fourier transformation for simplification of description. However, the process of generating the OCT tomographic image can be performed in any known method, and any signal processing can be performed on the interference signals in order to improve the image quality.

In Step S514, the image generation unit 210 checks whether n=N. If n=N, the image generation unit 210 proceeds to Step S515. If n<N, the image generation unit 210 increments n by 1 and repeats Step S513 as described above with regard to Step S512.

In Step S515, the tomographic image generation unit 213 aligns the N tomographic images associated with the scanning line position l with each other using characteristic points or the like in the tomographic images, such as the shape of the fundus Er in the tomographic images. As a result, the same part of the subject to be inspected is disposed at the same coordinates in the N tomographic images.

Specifically, the tomographic image generation unit 213 first selects any one of the N tomographic images as a template. For example, the tomographic image generation unit 213 can select the first generated tomographic image as the tomographic image to be selected as the template. Alternatively, the tomographic image generation unit 213 may calculate a correlation value for all the combinations of the N tomographic images, determine a sum of the correlation coefficients for each frame, and select a tomographic image for which the sum of the correlation coefficients is at the maximum, as a template.

The tomographic image generation unit 213 then compares each tomographic image against the template and determines a displacement amount ($\delta X$, $\delta Z$, $\delta \theta$) for each tomographic image. $\delta X$ denotes a displacement amount in the X direction, $\delta Z$ denotes a displacement amount in the Z direction, and $\delta \theta$ denotes a rotational displacement amount. Specifically, the tomographic image generation unit 213 calculates a normalized cross-correlation (NCC), which is an index of similarity of the template to the tomographic image of each frame, while changing the position and angle of the template. The tomographic image generation unit 213 determines, as the displacement amount, the difference in position between the template and the tomographic image to be compared at the time when the calculated NCC is at the maximum. The index of similarity between the images can be any measure of similarity of characteristics between the template and the tomographic image of the frame to be compared, and any of various indexes serving as such a measure can be used.

The tomographic image generation unit 213 aligns the tomographic images by applying a positional correction based on the determined displacement amount ($\delta X$, $\delta Z$, $\delta \theta$) to the N–1 tomographic images excluding the template. As a result of the N tomographic images being aligned with each other, the pixels at the same coordinates (pixel location) in the images represent the same part of the fundus Er. After the tomographic images are aligned with each other, the image generation unit 210 proceeds to Step S516.

In Step S516, the image generation unit 210 calculates motion contrast data, and selects a combination of tomographic images on which the threshold processing is to be performed. In Step S516, the image generation unit 210 first selects the first (n=1) tomographic image C(l, 1). The image generation unit 210 then proceeds to Step S517. After the process from Step S517 to Step S520 is ended, the image generation unit 210 compares n with N–1. If n is smaller than N–1, the image generation unit 210 increments n by 1 and repeats the process from Step S517 to Step S520.

In Step S517, the OCTA image generation unit 215 calculates a change in luminance value at each pixel location of the tomographic image corresponding to the motion contrast data at each pixel location from the tomographic image $C_{(l,\ n)}$ and the tomographic image $C_{(l,\ n+1)}$. In this exemplary embodiment, as the change in luminance value, a decorrelation value for the tomographic images is used. The decorrelation is calculated for each pair of pixels at the same coordinates (pixel location) of the tomographic images according to the following formula.

$$D_{(l,n)} = 1 - \frac{C_{(l,n)} C_{(l,n+1)}}{\frac{1}{2}(C_{(l,n)}^2 + C_{(l,n+1)}^2)}$$

As can be seen, the decorrelation value can be calculated by calculating a correlation value between the pixels at the same coordinates in the aligned tomographic images $C_{(l,\ n)}$ and $C_{(l,\ n+1)}$ and subtracting the correlation value from 1. A decorrelation value image $D_{(l,\ n)}$ can be calculated by calculating the decorrelation value for each pixel location.

In Step S518, the threshold calculation unit 214 calculates an optical shot noise threshold ths used for removing the decorrelation information generated by optical shot noise. The optical shot noise threshold ths is calculated for each pixel location (coordinates) in the tomographic image. The threshold calculation unit 214 takes an average of the luminance value for each pair of pixels at the same coordinates in the aligned tomographic images $C_{(l,\ n)}$ and $C_{(l,\ n+1)}$ to calculate an average value $C_{ave(l,\ n)}$ for each pixel location. Since the optical shot noise is proportional to the square root of the light intensity as described above, the square root $\sqrt{C_{ave(l,\ n)}}$ of the average value $C_{ave(l,\ n)}$ can be regarded as a standard deviation $C_{ave\_o(l,\ n)}$ of the optical shot noise. Therefore, the luminance value for each pair of pixels in the tomographic images $C_{(l,\ n)}$ and $C_{(l,\ n+1)}$ can be regarded as fluctuating with the standard deviation $C_{ave\_o(l, n)} = \sqrt{C_{ave(l, n)}}$. Thus, the threshold calculation unit 214 calculates a luminance value (first data) $CI_1 = C_{ave(l, n)} \alpha + \sqrt{C_{ave(l, n)}}$ and a luminance value (second data) $CI_2 = C_{ave(l, n)} - \alpha\sqrt{C_{ave(l, n)}}$. The threshold calculation unit 214 then calculates a decorrelation value between the luminance values $CI_1$ and $CI_2$ as the optical shot noise threshold ths for each pixel location.

α is an arbitrary coefficient and can be set according to the desired condition. However, α can generally be set at a value from 1 to 10. As α increases, a decorrelation value derived from the optical shot noise can be removed with higher reliability, although a decorrelation value due to an actual movement of a blood cell can be removed. On the other hand, as α decreases, the possibility that a decorrelation value due to an actual movement of a blood cell is removed decreases, although a decorrelation value derived from the optical shot noise is removed with lower precision. In general, the optical shot noise takes on a normal distribution, so that it can be considered that 99.7% of the luminance values derived from the optical shot noise falls within the range of ±3 times the standard deviation with respect to the average value. Thus, in this exemplary embodiment, α is set at 3, and the optical shot noise threshold ths that removes most of the decorrelation values calculated from the fluctuation in luminance value that are derived from the optical shot noise is calculated. The threshold calculation unit 214 can calculate the optical shot noise threshold ths for the tomographic images by calculating the optical shot noise threshold ths for each pixel location.

In Step S519, the OCTA image generation unit 215 determines that any decorrelation value equal to or smaller than the optical shot noise threshold ths is a decorrelation value due to the optical shot noise and is not a decorrelation value due to a movement of a blood cell. The OCTA image generation unit 215 compares the decorrelation value image $D_{(l, n)}$ with the optical shot noise threshold ths for the tomographic image for each pixel location, and maintains the decorrelation value as the pixel value at a pixel at a pixel location where the decorrelation value is greater than the optical shot noise ths. The OCTA image generation unit 215 sets the pixel value of a pixel at a pixel location where the decorrelation value is equal to or smaller than the optical shot noise threshold ths at 0. In this way, the OCTA image generation unit 215 generates a decorrelation value image $D'_{(l, n)}$ subjected to the optical shot noise threshold processing.

In Step S520, the OCTA image generation unit 215 then removes any decorrelation value derived from a change in luminance value due to the background noise. As described above, the probability of presence of the background noise has a probability distribution of concentric circles about an origin. Thus, any luminance value located outside a circle centered about the luminance value of 0 as an origin and having a radius that is the background noise threshold thn described above can be determined as a luminance value derived from the subject to be inspected. Therefore, the OCTA image generation unit 215 determines that the luminance value for any coordinates (pixel location) at which $Ic_n^2 + Ic_{n+1}^2 < thn^2$ is noise, where $Ic_n$ and $Ic_{n+1}$ denote the luminance values of the pixels at the same coordinates in the tomographic images $C_{(l, n)}$ and $C_{(l, n+1)}$, respectively.

Specifically, the OCTA image generation unit 215 determines whether or not luminance values $Ic_1$ and $Ic_2$ of the pixels at the same coordinates in the tomographic images $C_{(l, n)}$ and $C_{(l, n+1)}$ satisfy the relation $Ic_n^2 + Ic_{n+1}^2 < thn^2$ for the background noise threshold thn. If the relation $Ic_n^2 + Ic_{n+1}^2 < thn^2$ is satisfied, the OCTA image generation unit 215 sets the pixel value at the corresponding pixel location in the decorrelation value image $D'_{(l, n)}$ at 0. If the relation $Ic_n^2 + Ic_{n+1}^2 < thn^2$ is not satisfied, the OCTA image generation unit 215 maintains the decorrelation value at the corresponding pixel location in the decorrelation value image $D'_{(l, n)}$. If the background noise threshold thn is set for each pixel location, it is determined whether or not the luminance values $Ic_1$ and $Ic_2$ of the pixels at the same coordinates satisfy the relation $Ic_n^2 + Ic_{n+1}^2 < thn^2$ for the background noise threshold thn for the same coordinates.

By the processing described above, the OCTA image generation unit 215 can generate a motion contrast tomographic image (OCTA tomographic image) $Ac_{(l, n)}$ subjected to the optical shot noise threshold processing and the background noise threshold processing from the tomographic images $C_{(l, n)}$ and $C_{(l, n+1)}$.

In Step S521, the image generation unit 210 checks whether n=N−1. If n=N−1, the image generation unit 210 proceeds to Step S522. If n<N−1, the image generation unit 210 increments n by 1 and repeats the process from Step S517 to Step S520 as described above with regard to Step S516.

In Step S522, the OCTA image generation unit 215 calculates an average of the N OCTA tomographic images $Ac(l, 1), \ldots, Ac_{(l, N-1)}$ for each scanning line position 1, and calculates a final OCTA tomographic image $Ac_{(l)}$.

In Step S523, the image generation unit 210 checks whether l=L. If l=L, the image generation unit 210 ends the OCTA tomographic image generation processing and proceeds to Step S505. If l<L, the image generation unit 210 increments l by 1 and repeats the process from Step S512 to Step S522 as described above with regard to Step S511. In this way, the OCTA image generation unit 215 can calculate OCTA volume data in which motion contrast data (decorrelation values) is three-dimensionally arranged in the X, Y and Z directions.

In Step S505, the OCTA image generation unit 215 generates an OCTA image (OCTA front image) viewed in the normal direction to the XY plane based on the OCTA volume data. Specifically, the image generation unit 210 first performs a segmentation processing on the tomographic image selected as the template in Step S515 to extract a boundary of a layered structure of the fundus, which is the subject to be inspected. The layer boundaries can be extracted using any known layer boundary extraction technique, as far as the technique can extract an anatomical layer boundary of the fundus. Although the layer boundary extraction processing is performed in Step S505 in this exemplary embodiment, the layer boundary extraction processing can be performed at any time between completion of the tomographic image generation processing and Step S505. Alternatively, the image generation unit 210 may extract a layer boundary based on the tomographic data such as interference signals for the tomographic image. In that case, the layer boundary extraction processing can be performed at any time between acquisition of the tomographic data and Step S505.

Based on information on the extracted layer boundary, the OCTA image generation unit 215 generates an OCTA image in the XY plane based on the OCTA volume data for a desired structure of the subject to be inspected. For example, the OCTA image generation unit 215 generates the OCTA image in the XY plane by using an average in the depth direction (Z direction) of the pixel values in a region surrounded by the boundary between the retina and the vitreous body and the boundary between the ganglion cell layer and the inner plexiform layer as the pixel value at each location in the XY plane. The structure of the subject to be inspected for the volume data used for generation of the OCTA image can be any structure of the subject to be inspected included in the three-dimensional OCTA volume data. The pixel value of the OCTA image is not limited to the average value in the Z direction of the three-dimensional volume data and can be any representative value, such as the median, the maximum or the mode.

By the process described above, the control unit 200 can generate an OCTA image, which is a motion contrast image with high contrast, by performing appropriate threshold processes against the optical shot noise and the background noise.

Figure 6A:
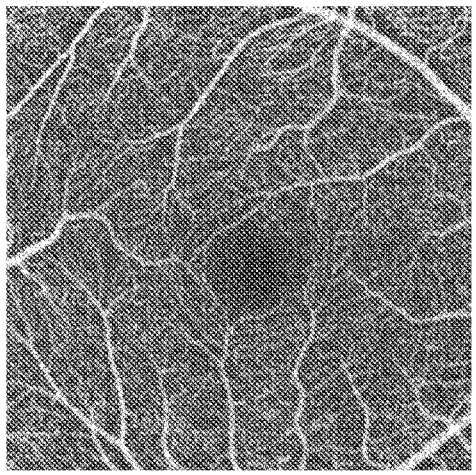
FIG. 6A shows an example of an OCTA image subjected to a conventional threshold processing.
Figure 6B:
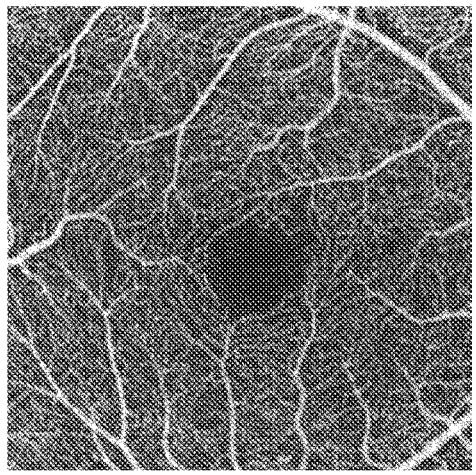
FIG. 6B shows an example of an OCTA image subjected to the conventional threshold processing and a threshold processing according to the first exemplary embodiment.
Figure 6C:
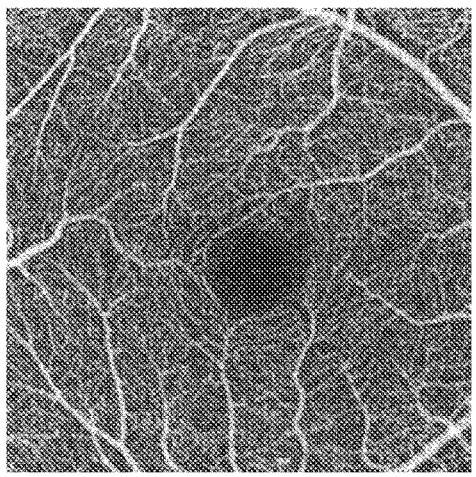
FIG. 6C shows an example of an OCTA image subjected to a threshold processing according to the first exemplary embodiment.
Figure 6D:
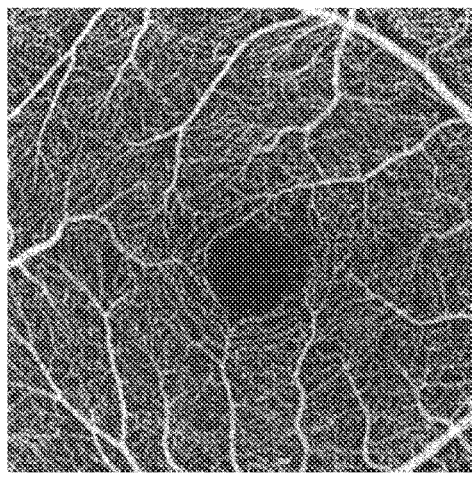
FIG. 6D shows an example of an OCTA image subjected to the threshold processes according to the first exemplary embodiment.

FIGS. 6A to 6D show OCTA images obtained by performing different threshold processes on the same tomographic data. FIG. 6A shows an OCTA image subjected to the conventional threshold processing, and FIG. 6B shows an OCTA image subjected to the conventional threshold processing and the optical shot noise threshold processing according to this exemplary embodiment. FIG. 6C shows an OCTA image subjected to the background noise threshold processing according to this exemplary embodiment, and FIG. 6D shows an OCTA image subjected to both the optical shot noise threshold processing and the background noise threshold processing according to this exemplary embodiment.

First, comparing FIGS. 6A and 6B, it can be seen that the image shown in FIG. 6A is low in contrast and looks white as a whole, although the image shown in FIG. 6B is higher in contrast and looks less white because the optical shot noise is appropriately treated. Comparing FIGS. 6A and 6C, it can be seen that the image shown in FIG. 6C is higher in contrast and the contours of the blood vessels are clearer because the background noise is appropriately treated. Comparing FIGS. 6A and 6D, it can readily be seen that the image shown in FIG. 6D looks less white is higher in contrast and the contours of the blood vessels are clearer because the optical shot noise and the background noise are appropriately treated. This result shows that the OCTA image can be generated with higher contrast when the threshold processes according to this exemplary embodiment are performed than when the conventional threshold processing is performed.

As described above, the control unit 200 includes the acquisition unit 220, the threshold calculation unit 214, and the OCTA image generation unit 215. The acquisition unit 220 acquires a plurality of pieces of tomographic data (a plurality of tomographic images) that indicates tomographic information on substantially the same part of the subject to be inspected. More specifically, the acquisition unit 220 acquires a plurality of pieces of tomographic data by performing optical coherence tomography of the subject to be inspected plural times by using the measuring light controlled to scan substantially the same part of the subject to be inspected. The threshold calculation unit 214 calculates a threshold from the luminance values of the pixels for which the decorrelation value (motion contrast data) is to be calculated in the plurality of pieces of tomographic data. The OCTA image generation unit 215 calculates the pixel values of the target pixels in the OCTA tomographic image (motion contrast image) based on the threshold and the decorrelation value calculated from the luminance values of the target pixels.

More specifically, the threshold calculation unit 214 calculates the first data $CI_1 = C_{ave} + \alpha \times \sqrt{C_{ave}}$ from the average value $C_{ave}$ of the luminance values of the target pixels in the plurality of pieces of tomographic data, the square root of the average value $C_{ave}$ and the coefficient $\alpha$. The threshold calculation unit 214 also calculates the second data $CI_2 = C_{ave} - \alpha \times \sqrt{C_{ave}}$ in the same manner. The threshold calculation unit 214 calculates the decorrelation value from the first data $CI_1$ and the second data $CI_2$ as the optical shot noise threshold ths. The threshold calculation unit 214 calculates an average value of two luminance values of the target pixels used for calculating the decorrelation value as the average value $C_{ave}$.

If the decorrelation value calculated from the luminance values of the target pixels is equal to or smaller than the optical shot noise threshold ths, the OCTA image generation unit 215 sets the pixel values of the target pixels of the OCTA tomographic image at 0. If the decorrelation value is greater than the optical shot noise threshold ths, the OCTA image generation unit 215 calculates the pixel values of the target pixels of the OCTA tomographic image using the decorrelation value.

Furthermore, the acquisition unit 220 acquires a plurality of pieces of background data of the imaging optical system 100 used for acquisition of the tomographic data on the subject to be inspected. The threshold calculation unit 214 calculates the background noise threshold $thn = N_{ave} + \beta \times N_\sigma$ from the average value $N_{ave}$ of the plurality of pieces of background data, and the standard deviation $N_\sigma$ and the coefficient $\beta$. Based on the background noise threshold thn, the OCTA image generation unit 215, for the values $Ic_1$ and $Ic_2$ of two pieces of tomographic data associated with the target pixels used for calculation of the decorrelation value, if the relation $Ic_1^2 + Ic_2^2 < thn^2$ is satisfied, the OCTA image generation unit 215 sets the pixel values of the target pixels at 0. If the relation $Ic_1^2 + Ic_2^2 < thn^2$ is not satisfied, the OCTA image generation unit 215 calculates the pixel values of the target pixels from the decorrelation value.

With such a configuration, the control unit 200 according to this exemplary embodiment can reduce the influence of the optical shot noise on the OCTA tomographic image and the OCTA image and generate a motion contrast image with higher contrast than when the conventional threshold processing is used.

Furthermore, if the luminance value of the pixel of one of the tomographic images is greater than the predetermined threshold, the control unit 200 according to this exemplary embodiment can use a change in luminance value of the pixel for generation of the OCTA image even if the luminance value of the pixel of the other tomographic image is not greater than the threshold. Therefore, the control unit 200 can provide a more appropriate background noise threshold processing and can generate a motion contrast image with higher contrast than when the conventional threshold processing is used.

Although the luminance value of the tomographic image is used for motion contrast data calculation, threshold calculation and threshold processing in this exemplary embodiment, the value used for these processes is not limited to the luminance value. These processes can be performed using tomographic data including an interference signal, a Fourier-transformed signal generated based on the interference signal, or this signal further subjected to some signal processing. Similarly, the background noise threshold thn does not always need to be generated from the luminance value of the background image, and may be generated based on the background signal acquired by the imaging optical system 100 or the background signal further subjected to the Fourier transformation or the like.

Furthermore, in this exemplary embodiment, the decorrelation value is determined as the motion contrast data.

However, the motion contrast data is not limited to the decorrelation value and may be any numerical value known as motion contrast data, such as the variance and the minimum value divided by the maximum value (minimum value/maximum value). If the OCTA image generation unit 215 uses the variance of the luminance values of the tomographic images as the motion contrast data, the threshold calculation unit 214 calculates a variance $C_{ave\_\sigma}^2$ ($=C_{ave}$) as the optical shot noise threshold ths. If the OCTA image generation unit 215 uses the minimum value/maximum value of the luminance values of the tomographic images as the motion contrast data, the threshold calculation unit 214 calculates $(C_{ave}-\sqrt{C_{ave}})/(C_{ave}+\sqrt{C_{ave}})$ as the optical shot noise threshold ths. In these cases, the OCTA image generation unit 215 performs the threshold processing on the motion contrast data determined from the tomographic images using the corresponding threshold.

Although the background noise threshold processing is performed after the optical shot noise threshold processing in this exemplary embodiment, the order of these threshold processes is not limited to this order. The background noise threshold processing may be performed before the optical shot noise threshold processing, or these threshold processes may be performed in parallel with each other. The timing when the background noise threshold is calculated is not limited to the timing described above, and the background noise threshold can be calculated after the background noise is acquired and before the background noise threshold processing is started.

In this exemplary embodiment, the threshold calculation unit 214 calculates the thresholds, and the OCTA image generation unit 215 performs various threshold processes using the calculated thresholds. Alternatively, the threshold calculation unit 214 may generate a mask that sets the pixel values of the target pixels at the pixel location at a value ranging from 0 to 1 according to the result of comparison between the calculated threshold and a comparison value.

For example, the threshold calculation unit 214 generates a mask that sets the pixel values at the pixel location of the target pixels at 0 if the decorrelation value is equal to or smaller than the optical shot noise threshold ths, and sets the pixel values at 1 if the decorrelation value is greater than the optical shot noise threshold ths. Similarly, the threshold calculation unit 214 generates a mask that sets the pixel values at the pixel location of the target pixels at 0 if the relation $Ic_n^2+Ic_{n+1}^2<thn^2$ is satisfied, and sets the pixel values at 1 if the relation $Ic_n^2+Ic_{n+1}^2<thn^2$ is not satisfied.

The OCTA image generation unit 215 calculates the pixel values of the target pixels of the OCTA tomographic images using the mask based on the thresholds and the decorrelation value. More specifically, the OCTA image generation unit 215 can generate a decorrelation value image subjected to the optical shot noise threshold processing by multiplying the decorrelation value image by the mask based on the optical shot noise threshold. Similarly, the OCTA image generation unit 215 can generate a decorrelation value image subjected to the background noise threshold processing by multiplying the decorrelation value image by the mask based on the background noise threshold. In this case, the same effects as in this exemplary embodiment can be achieved.

Modification of First Exemplary Embodiment

In the first exemplary embodiment, the average value of the luminance values of the pixels at each set of coordinates of the aligned tomographic images $C_{(l, n)}$ and $C_{(l, n+1)}$ and the square root of the average value are used to calculate the optical shot noise threshold ths. However, according to a modification of the first exemplary embodiment, an average value of the luminance values of the pixels at each set of coordinates of all of the N aligned tomographic images $C_{(l, 1)}, \ldots, C_{(l, N)}$ and the square root of the average value are used to calculate an optical shot noise threshold $ths_N$.

When the luminance values of two tomographic images are used as in the first exemplary embodiment, if the fluctuation of the optical shot noise is biased with respect to the luminance values derived from the fundus tissue, which is a subject to be inspected that does not move, the average value of the luminance values may significantly differ from the average value that would otherwise be obtained. Therefore, the optical shot noise threshold ths for each pixel may significantly differ from an appropriate value.

However, according to this modification, the average value is calculated from all the luminance values of the pixels at the same coordinates in the N tomographic images. By calculating the average value from the luminance values of all of the N tomographic images, the fluctuation of the measurement values is less likely to be biased, and a value closer to the value that would otherwise be measured from the fundus tissue is more likely to be obtained. Therefore, by using such an average value for calculation of the threshold, the optical shot noise threshold $ths_N$ is likely to be a more appropriate value. Therefore, the optical shot noise threshold processing can more appropriately remove any decorrelation value derived from the optical shot noise and more appropriately maintain any decorrelation value derived from a movement of the subject to be inspected, so that a motion contrast image with higher contrast can be generated.

In the first exemplary embodiment, the background noise processing is performed based on the luminance values $Ic_n$ and $Ic_{n+1}$ of the pixels at the same coordinates in the aligned tomographic images $C_{(l, n)}$ and $C_{(l, n+1)}$ and the background noise threshold thn. However, according to this modification, the background noise processing is performed based on the luminance values $Ic_1, \ldots, Ic_N$ of the pixels at the same coordinates in all of the N aligned tomographic images $C_{(l, 1)}, \ldots, C_{(l, N)}$ and the background noise threshold thn.

The background noise is distributed in the radial direction of a circle centered on an origin as described above, and the probability density of the noise is constant in the circumferential direction. This is not limited to the case where two tomographic images are used. Since the same apparatus acquires the tomographic images, even when three or more tomographic images are used, the background noise distributions in all the acquired tomographic images are the same and independent from each other.

For the sake of simplification of description, a case where three tomographic images are used will be described. Supposing that the luminance values of the pixels at the same coordinates in the three tomographic images are denoted by $I_1$, $I_2$ and $I_3$, the probability that the pixels at the coordinates are noise can be expressed as $P(I_1, I_2, I_3)$. In addition, since the luminance values in the different tomographic images are independent from each other, the probability can be expressed as follows.

$$P(I_1,I_2,I_3)=P(I_1)P(I_2)P(I_3)$$

$$P(I_1)P(I_2)P(I_3) \propto e^{-cI_1^2}e^{-cI_2^2}e^{-cI_3^2}=e^{-c(I_1^2+I_2^2+I_3^2)}=e^{-cr^2}$$

Thus, it can be seen that there is the same background noise distribution in the direction of the radius of a sphere. Thus, it can be seen that the probability density of the noise is the same on a spherical surface with a radius r.

As for luminance values $I_1, I_2, \ldots, I_N$ of the pixels at the same coordinates of N tomographic images, similarly, the following relation holds.

$$I_1^2+I_2^2+I_3^2+ \ldots +I_N^2=r^2$$

Thus, according to this modification, the background noise threshold determined in Step S502 is used as the value r, and the background noise threshold processing is performed based on the luminance values of the pixels at the same coordinates in the N tomographic images and the background noise threshold thn. In this threshold processing, an N-dimensional set of luminance values $(I_1, I_2, \ldots, I_N)$ located inside a circle having a radius r=thn is determined as the background noise. Therefore, in the background noise threshold processing according to this modification, the pixel values of the pixels at the coordinates in the decorrelation value image that correspond to the coordinates in the N tomographic images the set of luminance values at which is the background noise are set at 0, and the pixel values of the other pixels are maintained at the decorrelation values in the decorrelation value image to be processed.

As described above, whether the pixel value at each set of coordinates in the decorrelation value image is the background noise can be determined based on the luminance values of the N tomographic images, and the background noise can be more accurately identified. Therefore, the background noise threshold processing can more appropriately remove any decorrelation value derived from the background noise and more appropriately maintain any decorrelation value derived from a movement of the subject to be inspected (an object to be measured), so that an OCTA image with higher contrast can be generated.

According to this modification, the optical shot noise threshold can be generated based on more data and therefore can be more precisely calculated. According to this modification, the background noise threshold processing is performed using more data and therefore can be more precisely performed.

Figure 7:
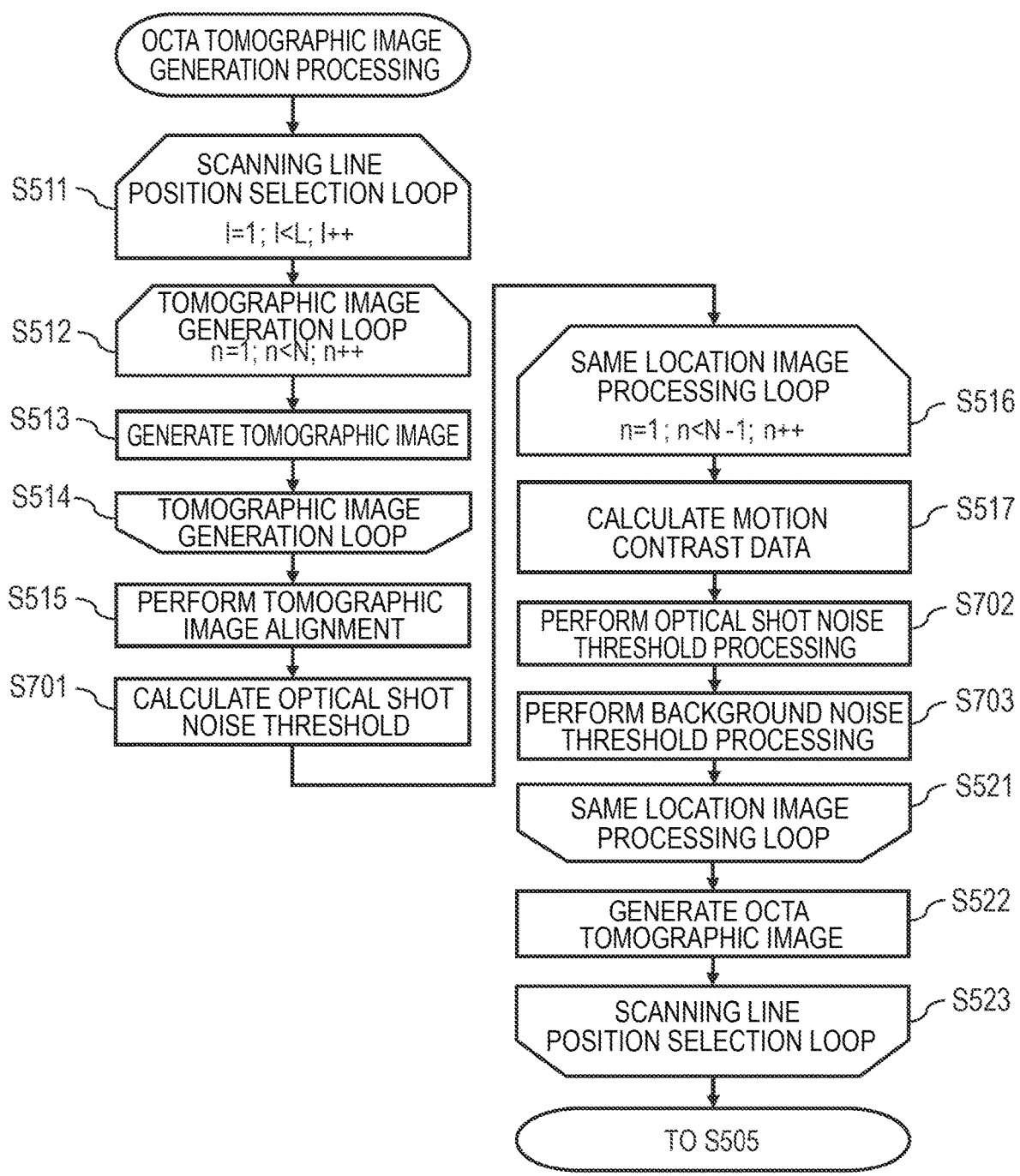
FIG. 7 shows a flow of an OCTA tomographic image generation processing according to a modification of the first exemplary embodiment.

In the following, with reference to FIG. 7, an image processing according to this modification will be described. The configuration of the OCT apparatus and the process excluding the threshold processes by the control unit are the same as those in the first exemplary embodiment, so that the differences from the first exemplary embodiment will be mainly described using the same reference numerals. FIG. 7 is a flowchart showing an OCTA tomographic image generation processing according to this modification.

In this modification, after the tomographic images are aligned with each other in Step S515, the image generation unit 210 proceeds to Step S701. In Step S701, the threshold calculation unit 214 takes an average of the luminance values of the pixels at the same coordinates in the N aligned tomographic images $C_{(l, 1)}$ to $C_{(l, N)}$ to calculate an average value $C_{ave(l)}$ for each pixel location. As in the first exemplary embodiment, the threshold calculation unit 214 designates the square root $\sqrt{C_{ave(l)}}$ of the average value $C_{ave(l)}$ as a standard deviation $C_{ave\_o(l)}$ of the optical shot noise. After that, the threshold calculation unit 214 calculates a decorrelation value between the luminance value (signal strength) $CI_1=C_{ave(l)}+\alpha\times\sqrt{C_{ave(l)}}$ and the luminance value $CI_2= C_{ave(l)}-\alpha\times\sqrt{C_{ave(l)}}$ as an optical shot noise threshold $ths_N$ for each pixel location.

After the threshold calculation unit 214 calculates the optical shot noise threshold $ths_N$, the image generation unit 210 proceeds to Step S516. After that, when the OCTA image generation unit 215 calculates the motion contrast data in Step S517, the image generation unit 210 proceeds to Step S702. In Step S702, as in Step S518 in the first exemplary embodiment, the OCTA image generation unit 215 performs the optical shot noise threshold processing on the calculated decorrelation value image $D_{(l, n)}$ using the optical shot noise threshold $ths_N$.

After the optical shot noise threshold processing is performed in Step S702, the image generation unit 210 proceeds to Step S703. In Step S703, the OCTA image generation unit 215 removes any decorrelation value derived from a change in luminance value due to the background noise. As described above, in this modification, using the luminance values $Ic_1, \ldots, Ic_N$ of the pixels at the same coordinates in the tomographic images $C_{(l, 1)}, \ldots, C_{(l, N)}$, the OCTA image generation unit 215 determines that the luminance value at any coordinates (pixel location) where the relation $Ic_1^2+ \ldots +Ic_N^2<thn^2$ is satisfied is noise.

Specifically, if the relation $Ic_1^2+ \ldots +Ic_N^2<thn^2$ is satisfied, the OCTA image generation unit 215 sets the pixel value at the corresponding pixel location in the decorrelation value image $D'_{(l, n)}$ at 0. If the relation $Ic_1^2+ \ldots +Ic_N^2<thn^2$ is not satisfied, the OCTA image generation unit 215 maintains the decorrelation value at the corresponding pixel location in the decorrelation value image $D'_{(l, n)}$.

By these processes, the OCTA image generation unit 215 can generate a motion contrast tomographic image (OCTA tomographic image) that is a decorrelation value image subjected to the optical shot noise threshold processing and the background noise threshold processing from the tomographic images $C_{(l, n)}$ and $C_{(l, n+1)}$. The subsequent process is the same as that in the first exemplary embodiment and therefore will not be further described.

As described above, according to this modification, the threshold calculation unit 214 calculates an average value of three or more pieces of tomographic data associated with the target pixels, in particular, all the luminance values of the target pixels in the N tomographic images as the average value $C_{ave}$. The OCTA image generation unit 215 determines whether the relation $Ic_1^2+Ic_2^2+ \ldots +Ic_N^2<thn^2$ is satisfied or not for the values $Ic_1, Ic_2, \ldots, Ic_N$ of all the tomographic data associated with the target pixels, based on the background noise threshold thn. If the relation $Ic_1^2+Ic_2^2+ \ldots +Ic_N^2<thn^2$ is satisfied, the OCTA image generation unit 215 sets the pixel values of the target pixels of the OCTA tomographic image at 0. If the relation $Ic_1^2+Ic_2^2+ \ldots +Ic_N^2<thn^2$ is not satisfied, the OCTA image generation unit 215 calculates the pixel values of the target pixels of the OCTA tomographic image from the motion contrast data.

In this modification, by using three or more pieces of tomographic data, in particular, all the N pieces of tomographic data, the precision of the optical shot noise threshold processing can be improved, and an OCTA image with higher contrast can be generated. Similarly, in this modification, by using N pieces of tomographic data, the precision of the background noise threshold processing can be improved, and an OCTA image with higher contrast can be generated.

Although whether the relation $Ic_1^2+ \ldots +Ic_N^2<thn^2$ is satisfied or not is determined for each pixel location when the background noise threshold processing is performed in this modification, the background noise threshold processing is not limited to this. For example, the threshold calculation unit 214 may generate a mask for the background noise threshold processing based on the tomographic images and the background noise threshold after the tomographic images are aligned with each other and before the background noise threshold processing is started.

Specifically, the threshold calculation unit 214 determines whether the luminance values of the pixels at each pixel location in the aligned tomographic images satisfy the relation $Ic_1^2 + \ldots + Ic_N^2 < thn^2$ or not. The threshold calculation unit 214 generates a mask that sets the pixel values in terms of luminance value at the pixel location in the tomographic images at 0 if the relation is satisfied, and sets the pixel values at 1 if the relation is not satisfied. In this case, in Step S703, the OCTA image generation unit 215 performs the background noise threshold processing by multiplying the generated mask for the background noise threshold processing by the decorrelation value image $D'_{(l,\,n)}$.

Such a process can also improve the precision of the background noise threshold processing and generate an OCTA image with higher contrast, as in this modification. Furthermore, once the mask is generated, the computational complexity of the background noise threshold processing can be reduced since the background noise threshold processing can be achieved by multiplying the decorrelation value image by the mask. Furthermore, as in the first exemplary embodiment, the threshold calculation unit 214 may generate a mask for the optical shot noise threshold.

Second Exemplary Embodiment

In the first exemplary embodiment, the optical shot noise threshold ths is calculated for each pixel location, and the optical shot noise threshold processing is performed on the decorrelation value image that is a motion contrast image. However, according to a second exemplary embodiment, a simpler method of calculating an optical shot noise threshold $ths_s$ will be described.

In the following, with reference to FIG. 8, a threshold processing according to this exemplary embodiment will be described. The configuration of the OCT apparatus and the process excluding the optical shot noise threshold processing according to this exemplary embodiment are the same as those in the first exemplary embodiment, so that the differences from the first exemplary embodiment will be mainly described using the same reference numerals.

In this exemplary embodiment again, the optical shot noise threshold $ths_s$ is calculated from the pixel values of the pixels at the same coordinates in two tomographic images used for generation of motion contrast data. FIG. 8 is a plot showing a distribution of luminance values of the two tomographic images, with the luminance value $I_1$ of the first tomographic image being indicated on the horizontal axis, the luminance value $I_2$ of the second tomographic image being indicated on the vertical axis, and each black dot indicating a set of luminance values at the same coordinates in the tomographic images. The tomographic images are arbitrarily selected, so that the black dots in the plot are in line symmetry with respect to a straight line passing through the origin and inclined by 45 degrees with respect to the horizontal and vertical axes, which is indicated by an alternate short and long dash line in the drawing. The quarter arc closer to the origin in the plot of FIG. 8 is a curve indicating the background noise threshold thn according to the first exemplary embodiment.

Figure 8:
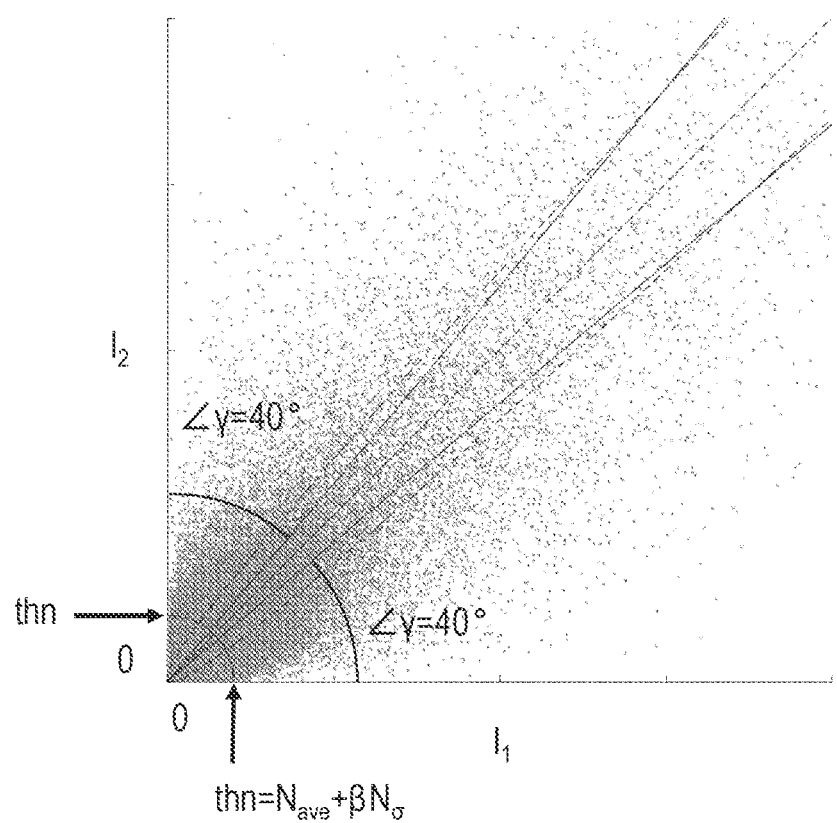
FIG. 8 is a diagram for illustrating a threshold according to a second exemplary embodiment.

In FIG. 8, of the sets of luminance values, sets of luminance values that correspond to the optical shot noise threshold ths according to the first exemplary embodiment are indicated by dashed lines. According to this exemplary embodiment, the optical shot noise threshold $ths_s$ indicated by a straight line in the plot is calculated in order to more simply set the optical shot noise threshold. In FIG. 8, the optical shot noise threshold $ths_s$ according to this exemplary embodiment is indicated by solid lines.

As described above, the sets of the luminance values of the pixels at the same coordinates in the two tomographic images used for generation of a motion contrast image are in line symmetry with respect to the straight line passing through the origin and inclined by 45° with respect to the horizontal and vertical axes in the plot of FIG. 8. Therefore, as shown in FIG. 8, the sets of luminance values that correspond to the optical shot noise threshold ths according to the first exemplary embodiment calculated from the average value of the luminance values of the pixels at the same coordinates in the two tomographic images and the square root of the average value are also in line symmetry with respect to the straight line inclined by 45 degrees. Thus, the optical shot noise threshold $ths_s$ according to this exemplary embodiment is also defined as straight lines that are substantially in line symmetry with respect to the straight line inclined by 45° in the plot. The phrase "substantially in line symmetry" includes a state where the threshold is slightly out of line symmetry.

Since these straight lines are in line symmetry with respect to the straight line passing through the origin and inclined by 45° with respect to the horizontal and vertical axes, two straight lines can be defined that form an angle γ with the horizontal and vertical axes, respectively. Therefore, in the plot of FIG. 8, the optical shot noise threshold ths according to this exemplary embodiment can be determined as two straight lines expressed by the following two formulas.

$$ths_{s1}: I_2 = \frac{I_1}{\tan\gamma} + I_0$$

$$ths_{s2}: I_2 = (I_1 - I_0)\tan\gamma$$

In these formulas, $I_0$ denotes an intercept of the straight line corresponding to the optical shot noise threshold $ths_{s2}$ on the $I_1$ coordinate axis and an intercept of the straight line corresponding to the optical shot noise threshold $ths_{s1}$ on the $I_2$ coordinate axis. In this exemplary embodiment, $I_0=0$, and the straight lines pass through the origin. The angle γ is an adjustment parameter and can be set at any angle depending on the desired configuration. As γ increases, the number of the luminance values regarded as fluctuations due to the optical shot noise and subjected to the threshold processing decreases. For example, γ may be adjusted while observing the final OCTA image subjected to the threshold processes. In this exemplary embodiment, γ=40°.

The straight lines determined in this exemplary embodiment substantially coincide with the curves (indicated by dashed lines in the drawing) of the optical shot noise threshold ths determined in the first exemplary embodiment with α=3 as shown in FIG. 8, so that the same effects can be expected. In the optical shot noise threshold processing according to this exemplary embodiment, it is determined whether or not the luminance values of the pixels at the same coordinates in the two tomographic images used for generation of the motion contrast image are sets of luminance values surrounded by the two straight lines determined according to the formulas described above. If the luminance values are sets of luminance values surrounded by the two straight lines, the luminance values are regarded as fluctuations of luminance values due to the optical shot noise, and the motion contrast data (decorrelation value) for the coordinates is set at 0. Otherwise, the decorrelation value is adopted as the pixel value.

In the following, a specific process flow according to this exemplary embodiment will be described. The process flow according to this exemplary embodiment is similar to the process flow according to the first exemplary embodiment, so that the description will be made with reference to FIG. 5B showing the process flow according to the first exemplary embodiment. The processes (steps) similar to those in the first exemplary embodiment will not be further described.

In this exemplary embodiment, in Step S518, the threshold calculation unit 214 calculates the optical shot noise threshold $ths_s$ based on one of the luminance values $Ic_{(l, n)}$ and the $Ic_{(l, n+1)}$ of the pixels at the same coordinates in the tomographic images $C_{(l, n)}$ and $C_{(l, n+1)}$. In the following description, it is supposed that the threshold calculation unit 214 calculates the optical shot noise threshold $ths_s$ based on the luminance value $Ic_{(l, n)}$ of the pixel in the tomographic image $C_{(l, n)}$.

The threshold calculation unit 214 calculates an optical shot noise threshold $ths_{s1}=Ic_{(l, n)}/\tan \gamma + I_0$ and an optical shot noise threshold $ths_{s2}=(Ic_{(l, n)}-I_0)\tan \gamma$ from the luminance value $Ic_{(l, n)}$ of the pixel. In this exemplary embodiment, $I_0=0$, and $\gamma=40°$. The threshold calculation unit 214 calculates the optical shot noise thresholds $ths_{s1}$ and $ths_{s2}$ for each pixel location in the tomographic image $C_{(l, n)}$.

In Step S519, the OCTA image generation unit 215 then performs the optical shot noise threshold processing using the luminance value $Ic_{(l, n+1)}$ at each pixel location in the tomographic image $C_{(l, n+1)}$ and the optical shot noise thresholds $ths_{s1}$ and $ths_{s2}$ for each pixel location. Specifically, the OCTA image generation unit 215 determines whether or not the luminance value $Ic_{(l, n+1)}$ at each pixel location in the tomographic image $C_{(l, n+1)}$ satisfies the relation $ths_{s2} \leq Ic_{(l, n+1)} \leq ths_{s1}$. If the relation $ths_{s2} \leq Ic_{(l, n+1)} \leq ths_{s1}$ is satisfied, the OCTA image generation unit 215 sets the pixel value at the pixel location in the decorrelation value image $D_{(l, n)}$ corresponding to the relevant pixel location at 0. If the relation $ths_{s2} \leq Ic_{(l, n+1)} \leq ths_{s1}$ is not satisfied, the OCTA image generation unit 215 maintains the pixel value at the pixel location in the decorrelation value image $D_{(l, n)}$ corresponding to the relevant pixel location. The subsequent process is the same as that in the first exemplary embodiment and therefore will not be further described.

By the processing described above, the control unit 200 according to this exemplary embodiment can generate an OCTA image with high contrast as with the control unit 200 according to the first exemplary embodiment. The same effects can also be achieved if, in Step S518, the optical shot noise threshold $ths_s$ is calculated based on the luminance value $Ic_{(l, n+1)}$ of the pixel in the tomographic image $C_{(l, n+1)}$. In that case, the threshold calculation unit 214 calculates the optical shot noise threshold $ths_{s1}=Ic_{(l, n+1)}/\tan \gamma + I_0$ and the optical shot noise threshold $ths_{s2}=(Ic_{(l, n+1)}-I_0)\tan \gamma$. Furthermore, in Step S519, the OCTA image generation unit 215 determines whether or not the luminance value $Ic_{(l, n)}$ at each pixel location in the tomographic image $C_{(l, n)}$ satisfies the relation $ths_{s2} \leq Ic_{(l, n)} \leq ths_{s1}$.

As described above, according to this exemplary embodiment, the threshold calculation unit 214 assumes a two-dimensional coordinate system whose coordinate axes indicate two tomographic data values $I_1$ and $I_2$ at the corresponding pixel location in a plurality of pieces of tomographic data. The threshold calculation unit 214 calculates two linear functions of $I_1$ with respect to value of $I_2$ that are substantially in line symmetry with respect to the straight line passing through the origin and inclined by 45° with respect to the respective coordinate axes as the first threshold $ths_{s1}$ and the second threshold $ths_{s2}$ ($ths_{s2} < ths_{s1}$). Specifically, the threshold calculation unit 214 calculates two linear functions of $I_1$ with respect to value of $I_2$, $ths_{s1}$: $I_2=I_1/\tan \gamma + I_0$ and $ths_{s2}$: $I_2=(I_1-I_0)\tan \gamma$, as the first threshold $ths_{s1}$ and the second threshold $ths_{s2}$. $I_0$ is an intercept of the linear function corresponding to the second threshold $ths_{s2}$ on the $I_1$ coordinate axis, and $\gamma$ is an angle formed by the linear function corresponding to the second threshold $ths_{s2}$ and the $I_1$ coordinate axis.

If the relation $ths_{s2} \leq I_2 \leq ths_{s1}$ is satisfied when the two tomographic data values corresponding to the target pixels used for calculation of the decorrelation value are substituted into the $I_1$ and $I_2$, the OCTA image generation unit 215 sets the pixel values of the target pixels of the OCTA tomographic images at 0. If the relation $ths_{s2} \leq I_2 \leq ths_{s1}$ is not satisfied, the OCTA image generation unit 215 calculates the pixel values of the target pixels in the OCTA tomographic images from the decorrelation value.

By these processes, the control unit 200 according to this exemplary embodiment can more simply calculate the optical shot noise threshold, and can generate an OCTA image with higher contrast as in the first exemplary embodiment even though the optical shot noise threshold processing is simpler.

As in the first exemplary embodiment, the threshold calculation unit 214 may generate a mask for a threshold processing of the decorrelation value image, which is a motion contrast image, using the optical shot noise threshold $ths_s$. Specifically, in Step S518, the threshold calculation unit 214 calculates the optical shot noise thresholds $ths_{s1}$ and $ths_{s2}$ from the luminance value $Ic_{(l, n)}$ of each pixel in one tomographic image $C_{(l, n)}$. Then, using the luminance value of the corresponding pixel in the other tomographic image $C_{(l, n+1)}$, the threshold calculation unit 214 generates a threshold mask that sets the pixel value at any pixel location where the relation $ths_{s2} \leq Ic_{(l, n+1)} \leq ths_{s1}$ is satisfied at 0 and sets the pixel value at any pixel location where the relation is not satisfied at 1. If the tomographic image $C_{(l, n+1)}$ is selected as the former tomographic image, the threshold calculation unit 214 uses the luminance value of the corresponding pixel in the other tomographic image $C_{(l, n)}$ to determine whether the relation $ths_{s2} \leq Ic_{(l, n)} \leq ths_{s1}$ is satisfied or not.

As described above, the optical shot noise threshold $ths_s$ removes (sets the pixel values at 0) the decorrelation values based on the sets of luminance values at the coordinates surrounded by the straight lines in a diagonal vicinity in the plot of the luminance values. Therefore, herein, the threshold generated using the optical shot noise threshold $ths_s$ is referred to as a diagonal vicinity threshold, and a mask for the threshold is referred to as a diagonal vicinity mask (DVM). When the diagonal vicinity mask is generated, in Step S519, the OCTA image generation unit 215 can perform the optical shot noise threshold processing by multiplying the decorrelation value image by the diagonal vicinity mask. In this case again, as in the case where the mask is not generated, the control unit 200 can generate an OCTA image with higher contrast.

The threshold calculation unit 214 can also calculate the optical shot noise threshold $ths_s$ for the optical shot noise threshold processing of N−1 motion contrast images by using N tomographic images. However, the optical shot noise threshold $ths_s$ according to this exemplary embodiment is not the average value of the luminance values or the standard deviation but relates to the distribution of sets of luminance values at pixel locations in two tomographic images used for generation of motion contrast data. In addition, the luminance values used for the final threshold processing are sets of luminance values at pixel locations in the two tomographic images used for generation of the motion contrast data. Therefore, even the optical shot noise threshold $ths_s$ calculated from N tomographic images can be determined for each of the sets of luminance values at pixel locations in two tomographic images by substituting the luminance values of the two tomographic images into the formulas.

Modification of Second Exemplary Embodiment

As the thresholds for the optical shot noise threshold processing and the background noise threshold processing, the noise threshold determined by the straight lines according to the second exemplary embodiment may be used alone. In this case, the background noise threshold thn is applied to $I_0$ in the formulas of the optical shot noise thresholds $ths_{s1}$ and $ths_{s2}$ described above.

Figure 9:
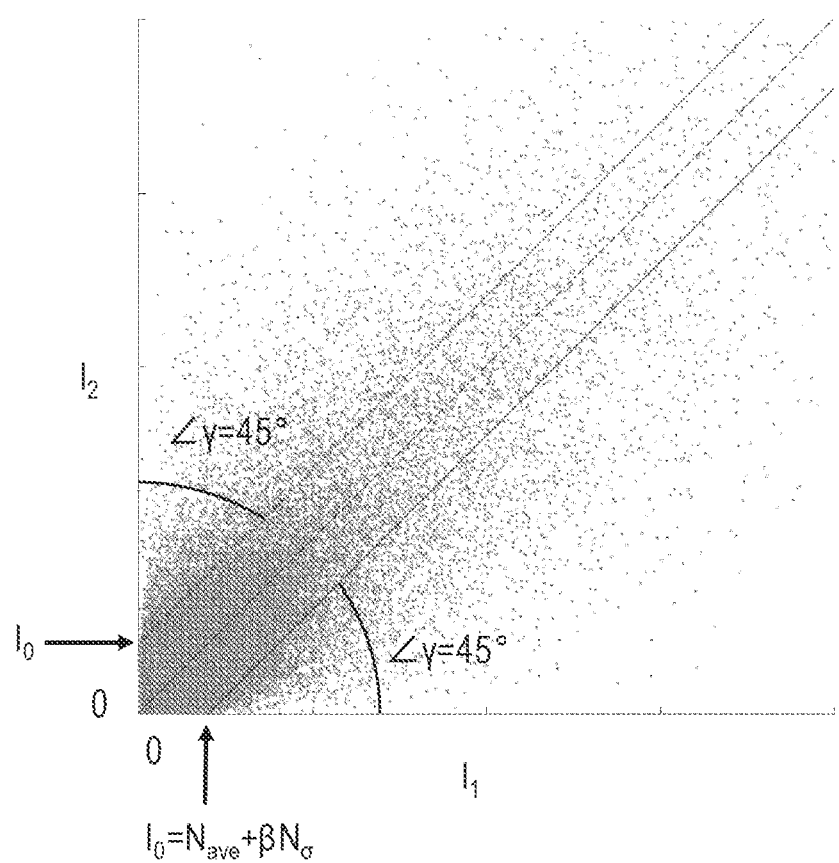
FIG. 9 is a diagram for illustrating a threshold according to a modification of the second exemplary embodiment.

FIG. 9 shows a plot of sets of luminance values $I_1$ and $I_2$ of two tomographic images used for generation of a motion contrast image. In FIG. 9, noise thresholds $tha_1$ and $tha_2$ according to this modification are indicated by solid lines. The formulas of the noise thresholds $tha_1$ and $tha_2$ are the same as those of the optical shot noise thresholds $ths_{s1}$ and $ths_{s2}$. In this modification, $\gamma=45°$, and $I_0=thn=N_{ave}+\beta \times N_\sigma$.

Figure 10A:
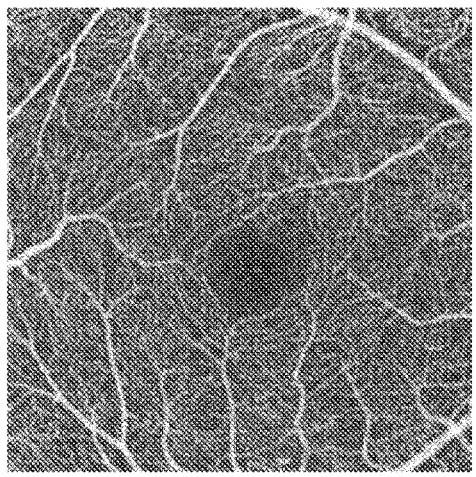
FIG. 10A shows an example of an OCTA image subjected to the conventional threshold processing.
Figure 10B:
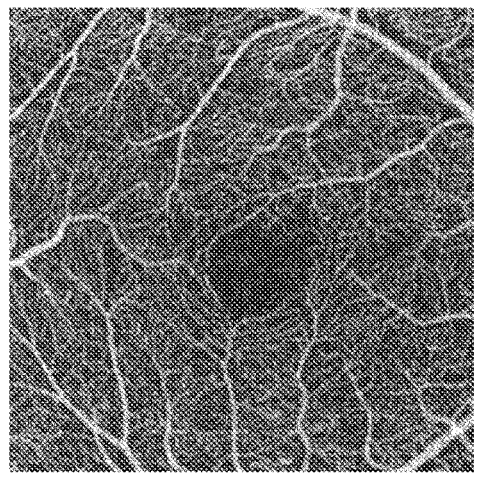
FIG. 10B shows an example of an OCTA image subjected to a threshold processing according to the modification of the second exemplary embodiment.

Comparing FIGS. 8 and 9, it can be seen that the range of the sets of luminance values surrounded by the straight line of the noise thresholds tha according to this modification covers, and is similar to, the range of the sets of luminance values that are considered as the background noise or optical shot noise according to second exemplary embodiment. Therefore, the effects of the threshold processing according to this modification are substantially the same as those of the threshold processing according to the second exemplary embodiment. FIG. 10A shows an OCTA image subjected to the conventional threshold processing, and FIG. 10B shows an OCTA image subjected to the threshold processing using the noise thresholds tha according to this modification. Comparing FIGS. 10A and 10B, it can be seen that the OCTA image in FIG. 10B looks less white as a whole and is improved in contrast.

The method of the threshold processing according to this modification is the same as that according to the second exemplary embodiment. Specifically, in Step S519, the threshold calculation unit 214 calculates the noise thresholds $tha_1$ and $tha_2$ according to the formulas of the optical shot noise thresholds $ths_{s1}$ and $ths_{s2}$ on the assumption that $I_0$=thn. That is, the threshold calculation unit 214 calculates the noise thresholds $tha_1=ths_{s1}=Ic_{(l, n)}/\tan \gamma+thn$ and the noise threshold $tha_2=ths_{s2}=(Ic_{(l, n+1)}-thn)\tan \gamma$. Then, in Step S520, the OCTA image generation unit 215 performs the threshold processing as in the second exemplary embodiment, by using the luminance values at each pixel location in the tomographic images and the noise thresholds that and $tha_2$. In this modification, the processing of Step S520 can be omitted, because the optical shot noise threshold includes the background noise threshold.

According to this modification, again, the diagonal vicinity mask (DVM) can be generated for the threshold processing. In this case, the optical shot noise threshold processing and the background noise threshold processing can be performed only by multiplying the decorrelation value image, which is a motion contrast image, by the generated diagonal vicinity mask (DVM).

According to this modification, again, the noise thresholds tha according to this modification for the noise threshold processing of N–1 motion contrast images ca be calculated by using N tomographic images. However, as in the second exemplary embodiment, the noise thresholds tha are also finally determined for the set of luminance values at each pixel location in the two tomographic images used for generation of the motion contrast data.

Third Exemplary Embodiment

With an ophthalmic imaging apparatus such as the OCT apparatus, even if imaging is performed under the same conditions, it is difficult to capture exactly the same images because of blinks of the eye of the patient, evaporation of tears, contraction/expansion of the pupil, and alignment change due to an eye movement. In particular, if these influences cause a significant difference in signal strength based on the reflection light from the subject to be inspected between the generated tomographic images, the tomographic images significantly differ in brightness.

In view of this, according to a third exemplary embodiment, there is provided a method of calculating an optical shot noise threshold, such as that determined in the second exemplary embodiment, and motion contrast data when there is a difference in brightness between two tomographic images. In the following, with reference to FIGS. 11 and 12, the method of calculating the optical shot noise threshold and the motion contrast data according to this exemplary embodiment will be described. The configuration of the OCT apparatus and the process excluding the optical shot noise threshold processing are the same as those in the second exemplary embodiment, so that the differences from the second exemplary embodiment will be mainly described using the same reference numerals.

Figure 11:
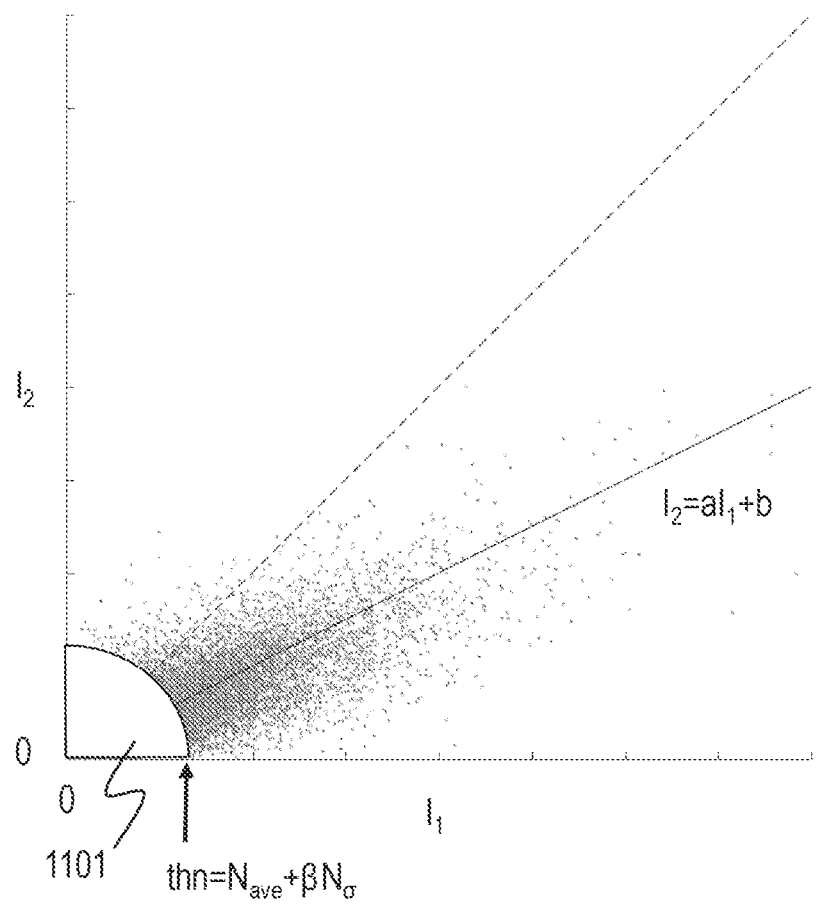
FIG. 11 is a diagram for illustrating a luminance value correction according to a third exemplary embodiment.

If the tomographic images significantly differ in brightness because of the influences described above, as shown in FIG. 11, the distribution of the sets of luminance values at pixel locations in the two tomographic images are biased toward the axis that indicates the luminance value of the tomographic image having higher luminance values as a whole. FIG. 11 is a plot showing the sets of luminance values at pixel locations in two tomographic images in the case where the two tomographic images used for generation of the motion contrast data significantly differ in brightness.

To the contrary, according to the second exemplary embodiment, the sets of luminance values are distributed substantially in line symmetry with respect to the diagonal line as shown in FIG. 8, since the two tomographic images have an equal brightness. Therefore, in the second exemplary embodiment, the formulas of the optical shot noise thresholds $ths_s$ can be expressed by the angle $\gamma$ formed by the straight lines indicating the thresholds and the respective axes and the luminance values (signal strengths) of the tomographic images.

However, if the distribution of the sets of luminance values of the two tomographic images is biased toward one of the axes as shown in FIG. 11, the distribution of the sets of luminance values is out of line symmetry with respect to the diagonal line (the straight line having a slope of 45° passing through the origin). Therefore, in such a case, if the luminance values of the tomographic images are used for calculation of the motion contrast data and the optical shot noise threshold as they are, the threshold processing cannot be appropriately achieved.

In view of this, according to this exemplary embodiment, in order that the same formulas as those in the second exemplary embodiment are used for the optical shot noise threshold processing, the brightness is corrected by multiplying the brightness of one of the tomographic images by a proportionality factor η so that the two tomographic images have an equal brightness.

Specifically, from the sets of luminance values $I_1$ and $I_2$ of the two tomographic images used for generation of the motion contrast data, sets of luminance values $I_1$ and $I_2$ that satisfy the relation $I_1^2+I_2^2<thn^2$ are removed, as in the background noise threshold processing according to the first exemplary embodiment. This is intended to prevent the background noise that is not affected by the change in brightness from being corrected, since the background noise is independent of the return light from the subject to be inspected and therefore does not change in luminance value of the background noise even if the brightness differs between the tomographic images. In this way, the sets of luminance values in a region 1101 in FIG. 11 are removed from the distribution of the set of luminance values $I_1$ and $I_2$.

Then, the distribution of the remaining sets of luminance values $I_1$ and $I_2$ are approximated to a straight line $I_2=aI_1+b$. Then, using an inverse of the slope a of the approximate straight line as the proportionality factor η, the luminance value $I_2$ is corrected according to the following formula to correct the brightness of the tomographic image.

$$I'_2 = \eta I_2 = \frac{1}{a} I_2$$

The luminance value $I_2$ at each pixel location is corrected in the same manner, thereby generating a tomographic image corrected in brightness. Then, using the tomographic image corrected in brightness and the other tomographic image, the motion contrast data and the optical shot noise thresholds $ths_s$ are calculated. By such a processing, the same optical shot noise threshold processing as in the second exemplary embodiment can be performed to generate an OCTA image with high contrast even when the two tomographic images used for generation of the motion contrast data significantly differ in brightness.

Figure 12:
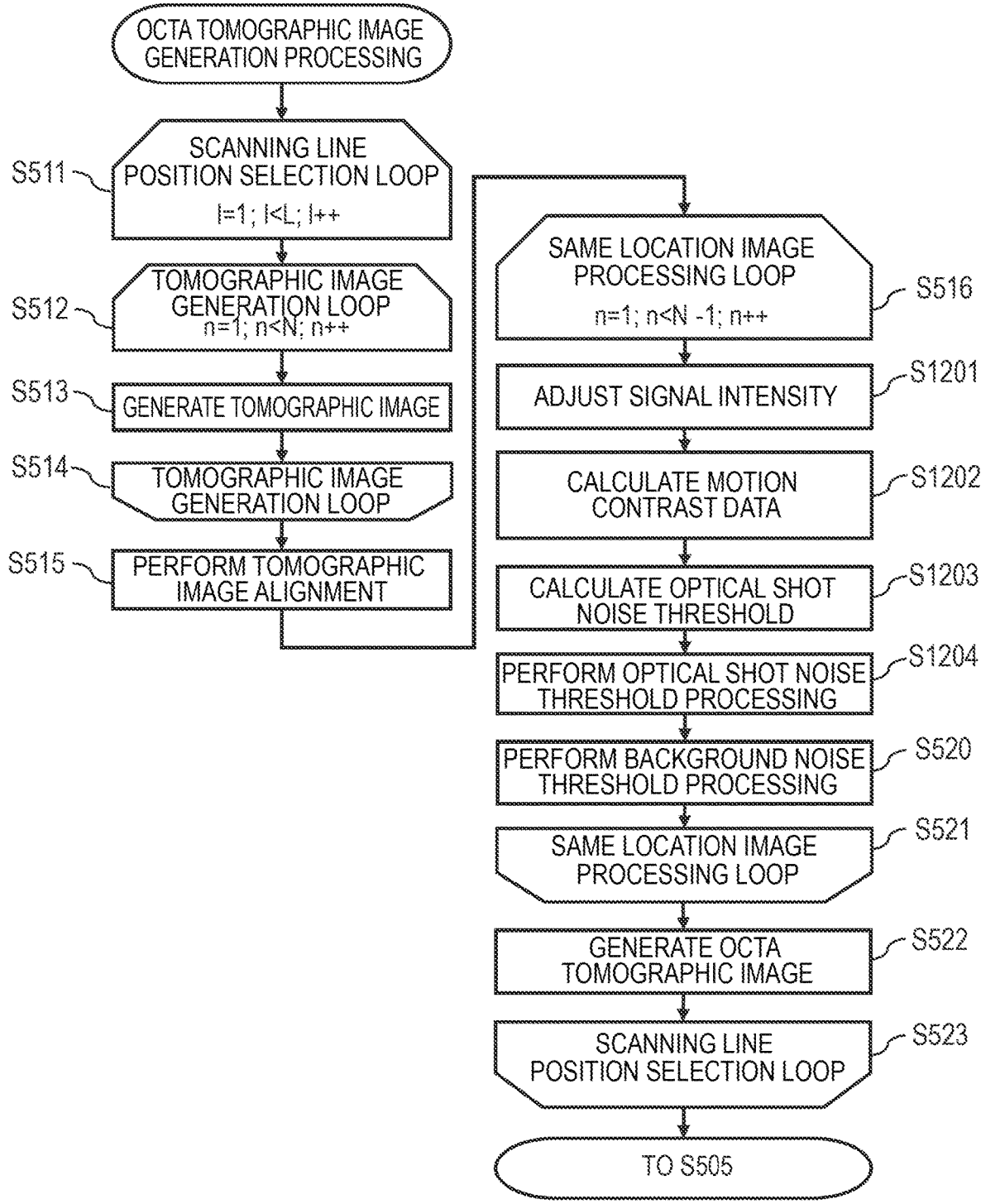
FIG. 12 shows a flow of an OCTA tomographic image generation processing according to the third exemplary embodiment.

In the following, with reference to FIG. 12, a flow of an OCTA tomographic image generation processing including a signal strength adjustment processing, an optical shot noise threshold processing and the like according to this exemplary embodiment will be described. FIG. 12 is a flowchart showing the OCTA tomographic image generation processing according to this exemplary embodiment. The steps in which the same processes as those in the second exemplary embodiment are performed will not be further described.

After the image processing loop for the same part is started in Step S516, the image generation unit 210 proceeds to Step S1201. In Step S1201, the OCTA image generation unit 215 performs strength adjustment on the set of luminance values (signal strengths) $Ic_{(l,n)}$ and $Ic_{(l,n+1)}$ of the two tomographic images $C_{(l,n)}$ and $C_{(l,n+1)}$ used for generation of the motion contrast data.

Specifically, as in the background noise threshold processing according to the first exemplary embodiment, the OCTA image generation unit 215 first removes the sets of luminance values $Ic_n$ and $Ic_{n+1}$ that satisfy the relation $Ic_{(l,n)}^2 + Ic_{(l,n+1)}^2 < thn^2$ from the sets of luminance values $Ic_{(l,n)}$ and $Ic_{(l,n+1)}$.

Then, the OCTA image generation unit 215 approximates the distribution of the remaining sets of luminance values $Ic_{(l,n)}$ and $Ic_{(l,n+1)}$ to a straight line $Ic_{(l,n+1)} = aIc_{(l,n)} + b$. Furthermore, the OCTA image generation unit 215 determines the proportionality factor η=1/a from the slope a of the approximate straight line, and corrects the luminance values $Ic_{(l,n+1)}$ according to $Ic_{(l,n+1)}' = \eta Ic_{(l,n+1)}$. The OCTA image generation unit 215 performs this processing on the pixel at each pixel location in the tomographic image $C_{(l,n+1)}$, thereby generating a tomographic image $C_{(l,n+1)}'$ corrected in brightness.

In Step S1202, as in the second exemplary embodiment, the OCTA image generation unit 215 then calculates the decorrelation value image $D_{(l,n)}$ from the tomographic image $C_{(l,n)}$, and the tomographic image $C_{(l,n+1)}'$ corrected in brightness. In Step S1203, as in the second exemplary embodiment, the threshold calculation unit 214 calculates the optical shot noise threshold $ths_s$ from the tomographic image $C_{(l,n)}$ and the tomographic image $C_{(l,n+1)}'$ corrected in brightness. In Step S1204, as in the second exemplary embodiment, the OCTA image generation unit 215 then performs the same optical shot noise threshold processing using the tomographic image $C_{(l,n)}$, the tomographic image $C_{(l,n+1)}'$ corrected in brightness and the optical shot noise threshold $ths_s$.

The subsequent process is the same as that in the second exemplary embodiment and therefore will not be further described. In Step S520, since the background noise is not affected by the change in light quantity of the return light from the subject to be inspected as described above, the OCTA image generation unit 215 performs the threshold processing using the tomographic images $C_{(l,n)}$ and $C_{(l,n+1)}$ and the background noise threshold thn.

As described above, according to this exemplary embodiment, the OCTA image generation unit 215 corrects the magnitude of the tomographic data values of the two pieces of tomographic data that correspond to the target pixels used for calculation of the decorrelation value. Therefore, the OCTA image generation unit 215 functions as a correction unit that corrects the magnitude of the tomographic data value. The OCTA image generation unit 215 plots the distribution of sets of tomographic data in the two-dimensional coordinate system whose coordinate axes indicate the tomographic data values $Ic_1$ and $Ic_2$, provided that $Ic_1$ denotes the value of one of the tomographic data, and $Ic_2$ denotes the value of the other tomographic data. The OCTA image generation unit 215 calculates the approximate straight line $Ic_2=aIc_1+b$, which is an approximation of the distribution of the sets of tomographic data obtained by removing the distribution corresponding to the background noise from the distribution of the sets of tomographic data used for calculation of the decorrelation value. The OCTA image generation unit 215 calculates the factor η according to η=1/a and corrects the tomographic data value $Ic_2$ according to $Ic_2' = \eta \times Ic_2$.

The threshold calculation unit 214 calculates the optical shot noise threshold ths from the tomographic data values $Ic_1$ of the target pixels and the corrected tomographic data values $Ic_2'$. The OCTA image generation unit 215 calculates the pixel values of the target pixels in the OCTA tomographic image based on the decorrelation value calculated from the optical shot noise threshold ths, the tomographic data values $Ic_1$ of the target pixels and the corrected tomographic data values $Ic_2'$.

According to this exemplary embodiment, even if the tomographic images used for calculation of the motion contrast data differ in brightness, an OCTA tomographic image with high contrast can be generated by adjusting the brightness of the tomographic images. Although this exemplary embodiment has been described in the context of the brightness of the tomographic image, the quantity that needs correction is not limited to brightness. The quantity that needs correction can be any tomographic data value used for calculation of the motion contrast data. In other words, according to this exemplary embodiment, an OCTA tomographic image with high contrast can be generated by correcting an overall difference in any quantity between the tomographic data.

In the correction of the brightness according to this exemplary embodiment, the luminance value $Ic_{(l,\ n+1)}$ of the tomographic image $C_{(l,\ n+1)}$ is corrected in Step S1201. Alternatively, the luminance value $Ic_{(l,\ n)}$ of the tomographic image $C_{(l,\ n)}$ may be corrected to generate a tomographic image $C_{(l,\ n)}$ corrected in brightness. In that case, the OCTA image generation unit 215 calculates an approximate straight line $Ic_{(l,\ n)} = aIc_{(l,\ n+1)} + b$ and determines the proportionality factor $\eta = 1/a$. The OCTA image generation unit 215 then corrects the luminance value $Ic_{(l,\ n)}$ according to $Ic_{(l,\ n)}' = \eta Ic_{(l,\ n)}$. The OCTA image generation unit 215 then performs this processing on the pixel at each pixel location in the tomographic image $C_{(l,\ n)}$, thereby generating a tomographic image $C_{(l,\ n)}'$ corrected in brightness. After that, using the tomographic image $C_{(l,\ n+1)}$ and the tomographic image $C_{(l,\ n)}'$ corrected in brightness, the optical shot noise threshold $ths_s$ is calculated, and the optical shot noise threshold processing is performed.

For the optical shot noise threshold according to this exemplary embodiment, again, the diagonal vicinity mask (DVM) may be generated. Similarly, as the threshold processing according to this exemplary embodiment, the threshold processing according to the modification of the second exemplary embodiment (including the case where the mask is generated) may be applied.

The correction of the brightness may be performed as required. For example, before Step S1201, the average value of the luminance values or the like may be compared between the two tomographic images $C_{(l,\ n)}$ and $C_{(l,\ n+1)}$ used for generation of the motion contrast data. If the comparison result shows that the difference between the two tomographic images is equal to or smaller than a predetermined threshold, Step S1201 may be omitted.

Fourth Exemplary Embodiment

It is generally known that an artifact referred to as a projection artifact occurs in the OCTA image at a part where the luminance value of the tomographic image is equal to or higher than a certain level. The projection artifact is remarkable in a layer rendered with higher luminance in the OCT tomographic image, such as the interface between the inner segment and the outer segment (IS/OS) of the visual cells in the retina of the fundus and the pigment epithelium (RPE). The projection artifact occurs in the form of a pixel with higher luminance due to a movement of a blood cell in a layer below the layers described above. According to a fourth exemplary embodiment, a threshold processing is performed on motion contrast data corresponding to a pixel of a tomographic image that has a luminance value equal to or higher than a certain level.

If a pixel whose motion contrast value is 0 is used when averaging of the OCTA tomographic image is performed or when the OCTA tomographic image is generated, the final motion contrast value is too small. According to this exemplary embodiment, when averaging of the OCTA tomographic image is performed or when the OCTA image is generated, averaging is performed by ignoring any pixel whose motion contrast value (pixel value) is rewritten as 0 by the threshold processing.

Figure 13:
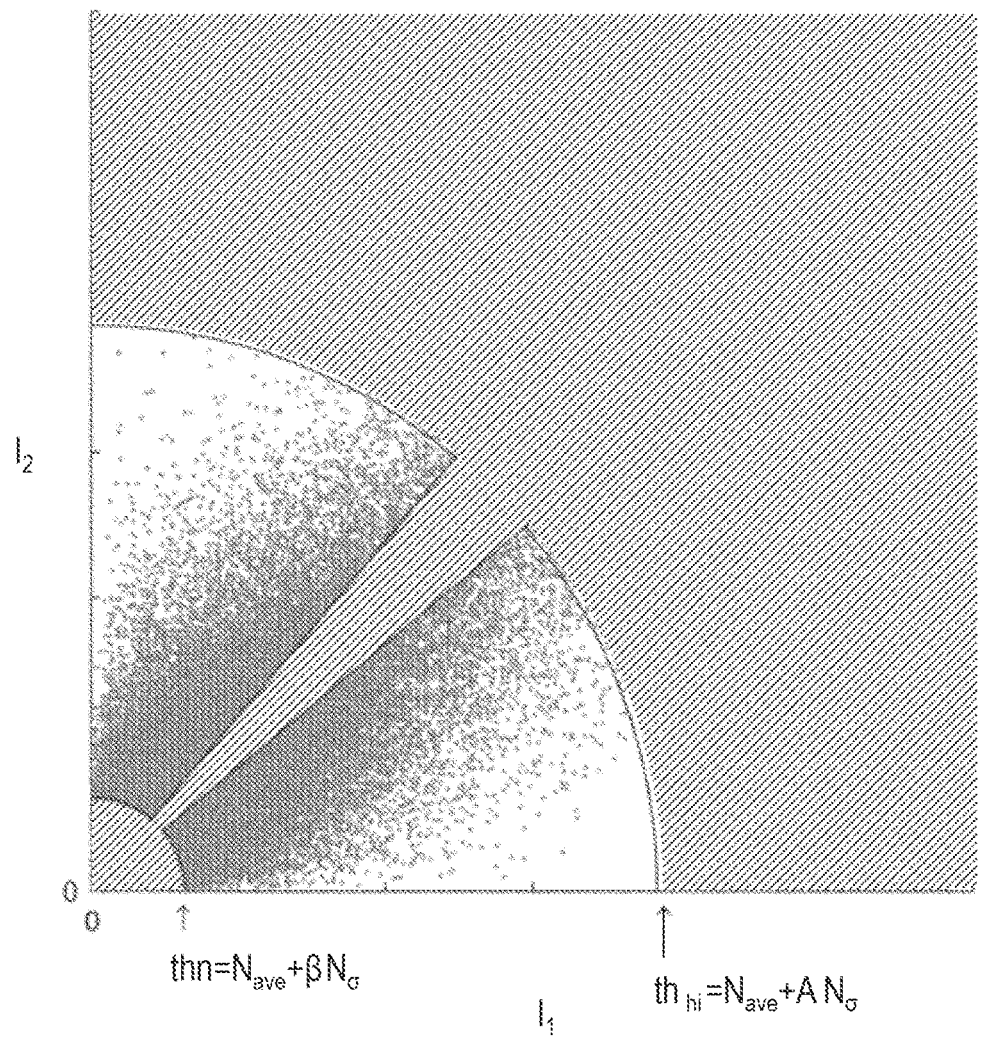
FIG. 13 is a diagram for illustrating a threshold according to a fourth exemplary embodiment.

In the following, with reference to FIGS. 13 and 14, a method of calculating a high-value threshold processing according to this exemplary embodiment will be described. The configuration of the OCT apparatus and the process excluding the optical shot noise threshold processing according to this exemplary embodiment are the same as those in the second exemplary embodiment, so that the differences from the second exemplary embodiment will be mainly described using the same reference numerals.

According to this exemplary embodiment, the image generation unit 210 performs the high-value threshold processing for suppressing the projection artifact. In the high-value threshold processing, the threshold calculation unit 214 determines a high-value threshold $th_{hi} = N_{ave} + A \times N_\sigma$ from the average value $N_{ave}$ and the standard deviation $N_\sigma$ of the background noise. The OCTA image generation unit 215 then determines whether or not the luminance values $I_1$ and $I_2$ at each pixel location in the two tomographic images used for generation of the motion contrast data satisfy the relation $I_1^2 + I_2^2 > th_{hi}^2$. If the relation $I_1^2 + I_2^2 > th_{hi}^2$ is satisfied, the OCTA image generation unit 215 sets the pixel value at any pixel location in the decorrelation value image that corresponds to the relevant pixel location at 0. If the relation $I_1^2 + I_2^2 > th_{hi}^2$ is not satisfied, the pixel value at any pixel location in the decorrelation value image that corresponds to the relevant pixel location is maintained.

In this way, the projection artifact rendered in the OCTA image including a high-luminance layer such as IS/OS and RPE due to the influence of a layer in the fundus can be suppressed without degradation of the OCTA image. FIG. 13 shows a distribution of sets of luminance values at pixel locations in the two tomographic images that correspond to the pixel values of the final decorrelation value image. According to this exemplary embodiment, the background noise region, the optical shot noise region, and a high-luminance region that causes the projection artifact are removed from the distribution of sets of luminance values at pixel locations in the two tomographic images that correspond to the pixel values of the final decorrelation value image. As a result, an OCTA image with high contrast in which the background noise, the optical shot noise and the projection artifact are reduced can be generated. In FIG. 13, the regions to be removed are shown as hatched regions.

According to this exemplary embodiment, the OCTA image generation unit 215 ignores any pixel whose motion contrast value is rewritten as 0 by the threshold processing, when taking an average of the OCTA tomographic images (decorrelation value images). Furthermore, the OCTA image generation unit 215 generates the OCTA image by ignoring any pixel whose motion contrast value is rewritten as 0 by the threshold processing when taking an average of the motion contrast values in the depth direction of a desired region of the subject to be inspected based on the layer boundary.

As a result, the quality of the OCTA image can be improved without producing a too small average value of the motion contrast values in the averaging process for the motion contrast values.

In the following, with reference to FIG. 14, a flow of the OCTA tomographic image generation processing including the high-value threshold processing and the averaging processing (removal processing) of the motion contrast values according to this exemplary embodiment will be described.

FIG. 14 is a flowchart of the OCTA tomographic image generation processing according to this exemplary embodiment. The steps in which the same processes as those in the second exemplary embodiment are performed will not be further described.

In the OCTA tomographic image generation processing according to this exemplary embodiment, after the background noise threshold processing is performed in Step S520, the process proceeds to Step S1401. In Step S1401, the threshold calculation unit 214 determines the high-value threshold $th_{hi}=N_{ave}+A\times N_o$ from the average value $N_{ave}$ and the standard deviation $N_o$ of the background noise calculated in Step S502. The coefficient A can be any value. For example, the coefficient A can be adjusted while observing the final OCTA image subjected to the threshold processing so that the projection artifact is reduced.

In Step S1402, the OCTA image generation unit 215 determines whether or not the luminance values $Ic_{(l, n)}$ and $Ic_{(l, n+1)}$ at the same coordinates in the two tomographic images $C_{(l, n)}$ and $C_{(l, n+1)}$ satisfy the relation $Ic_{(l, n)}^2 + Ic_{(l, n+1)}^2 > th_{hi}^2$. If the relation $Ic_{(l, n)}^2 + Ic_{(l, n+1)}^2 > th_{hi}^2$ is satisfied, the OCTA image generation unit 215 sets the pixel value at any pixel location in the decorrelation value image that corresponds to the relevant coordinates (pixel location) at 0. On the other hand, if the relation $Ic_{(l, n)}^2 + Ic_{(l, n+1)}^2 > th_{hi}^2$ is not satisfied, the OCTA image generation unit 215 maintains the pixel value at any pixel location in the decorrelation value image that corresponds to the relevant coordinates.

Then, after the image processing loop for the same part is completed in Step S521, the image generation unit 210 proceeds to Step S1403. In Step S1403, when the OCTA image generation unit 215 takes an average of the pixel values at each pixel location in the N−1 decorrelation value images, the pixel value of any pixel whose pixel value is set at 0 in the threshold processing is omitted from the averaging processing. Specifically, the OCTA image generation unit 215 omits the pixel value of any pixel whose pixel value is set at 0 in Steps S519, S520 and S1402 from the averaging processing. Then, the OCTA image generation unit 215 generates an OCTA tomographic image using the averaged pixel values.

For the pixels whose pixel values are set at 0 in Steps S519, S520 and S1402, the locations of the pixels whose pixel values are set at 0 may be stored in the storage 240 in the respective threshold processes. In that case, the OCTA image generation unit 215 omits the pixel values whose locations are stored in the storage 240 from the averaging processing. The OCTA image generation unit 215 may identify, by another processing, the locations of the pixels whose pixel values are set at 0 in the respective threshold processes.

After the OCTA tomographic image generation processing is completed, in Step S505, the OCTA image generation unit 215 generates the OCTA image (OCTA front image) from the three-dimensional OCTA volume data based on the generated OCTA tomographic image. The OCTA image generation unit 215 generates the OCTA image by ignoring any pixel whose motion contrast value is rewritten as 0 by the threshold processing when taking an average of the motion contrast values in the depth direction of a desired region of the subject to be inspected based on the layer boundary.

Specifically, the OCTA image generation unit 215 omits the pixel value of any pixel of the three-dimensional OCTA volume data whose pixel value is set at 0 in Steps S519, S520 and S1402 from the averaging processing. The desired region of the subject to be inspected can be arbitrarily set in each OCTA tomographic image and can be a region surrounded by the boundary between the retina and the vitreous body and the boundary between the ganglion cell layer and the inner plexiform layer, for example. The pixels whose pixel values are set at 0 in Steps S519, S520 and S1402 can be identified by reading the locations of the pixels stored in the storage 240 in the respective threshold processes as in Step S1403. The locations of the pixels whose pixel values are set at 0 in the respective threshold processes may be identified by another processing.

Even when the mode or median rather than the average value is calculated and used as the pixel value when generating the OCTA image, the pixels whose pixel values are set at 0 in the threshold processings can be omitted from calculation in the same manner as described above.

As described above, according to this exemplary embodiment, the acquisition unit 220 acquires a plurality of pieces of background data on the imaging optical system 100 used for acquisition of the tomographic data on the subject to be inspected. Furthermore, the threshold calculation unit 214 calculates the high-value threshold $th_{hi}=N_{ave}+A\times N_o$ from the average value $N_{ave}$ and the standard deviation $N_o$ of a plurality of pieces of background data and the coefficient A. Based on the high-value threshold $th_{hi}$, the OCTA image generation unit 215 sets the pixel values of the target pixels of the OCTA tomographic images at 0 if the relation $Ic_1^2 + Ic_2^2 > th_{hi}^2$ is satisfied for the tomographic data values $Ic_1$ and $Ic_2$ of the target pixels. If the relation $Ic_1^2 + Ic_2^2 > th_{hi}^2$ is not satisfied, the OCTA image generation unit 215 calculates the pixel values of the target pixels of the OCTA tomographic images from the decorrelation values.

When taking an average of a plurality of motion contrast images the pixel values of the target pixels of which are calculated, the OCTA image generation unit 215 omits the pixel values of the target pixels whose pixel values are set at 0 based on the threshold from the averaging processing.

According to this exemplary embodiment, the projection artifact that is likely to occur in a layer that is rendered with high luminance in the tomographic image can be suppressed, and the quality of the OCTA image can be improved by ignoring the pixels whose pixel values are set at 0 in the threshold processing when performing the averaging processing.

The high-value threshold processing according to this exemplary embodiment can also be performed by generating a mask image based on the luminance value of the tomographic image and the high-value threshold. Furthermore, although this exemplary embodiment has been described with reference to the second exemplary embodiment, the high-value threshold processing and the averaging processing (removal processing) according to this exemplary embodiment can also be applied to the first exemplary embodiment, the third exemplary embodiment, and the modifications of the first and second exemplary embodiments. Furthermore, the order of the threshold processing is not limited to the order described above. The high-value threshold processing may be performed before one of the optical shot noise threshold processing and the background noise threshold processing or in parallel with these processes.

Modifications of Various Threshold Processes

In the exemplary embodiments and modifications thereof, the threshold processes have two possible results: the pixel value is set at 0 or the pixel value at the target pixel location is maintained. However, the threshold may have a boundary margin, and the pixel value at the target pixel location may be multiplied by a value ranging from 0 to 1.

For example, the background noise threshold thn in the first exemplary embodiment may have a margin of δr in the radial direction, and the motion contrast value at coordinates where the relation $thn^2-(\delta r/2)^2 < I_1^2+I_2^2 < thn^2+(\delta r/2)^2$ holds may be multiplied by a weight w that linearly changes between 0 and 1. In this case, the weight w is set to come closer to 1 as $I_1^2+I_2^2$ comes closer to $thn^2+(\delta r/2)^2$. Similarly, other thresholds can have a margin.

More specifically, the threshold calculation unit 214 sets a margin δ for the calculated threshold. Then, if the value compared with the threshold falls within the range of ±δ with respect to the threshold, the OCTA image generation unit 215 calculates, as the pixel value, the decorrelation value multiplied by the weigh w ranging from 0 to 1 that comes closer to 1 as the compared value deviates from the noise region. In this way, the threshold processing can be performed by considering signals locating on the noise region side of the threshold and noises located on the signal region side of the threshold. When a mask is generated for the threshold as described above, the same effects can be achieved by setting the pixel value of the mask at a value ranging from 0 to 1 according to the boundary margin of the threshold.

As described above, according to the exemplary embodiments and modifications thereof, motion contrast values derived from the optical shot noise and the background noise can be removed by the threshold calculated from the signal strength of the pixels at the same coordinates in a plurality of aligned tomographic images. As a result, a motion contrast image with high contrast can be provided.

The user of the apparatus may change the parameters, such as the thresholds, described above in the exemplary embodiments on a GUI with a mouse or a keyboard. As specific examples, various relevant parameters, such as the coefficient α of the optical shot noise threshold, the coefficient β of the background noise threshold, the angle γ of the diagonal vicinity threshold associated with the optical shot noise, the coefficient A of the high-value threshold, and the boundary margin δ of the threshold described above, can be changed.

The processes according to the exemplary embodiments and modifications thereof described above are not limited to those performed based on the luminance value of the tomographic image. The various processes described above can be applied to tomographic data including an interference signal acquired in the imaging optical system 100, the interference signal Fourier-transformed, this signal further subjected to an arbitrary processing, and a tomographic image based on these signals, for example. In those cases, the same effects as those achieved by the configurations described above can be achieved. The motion contrast data is not limited to the decorrelation value described above, and may be any value known as the motion contrast data, such as the variance or the minimum value divided by the maximum value of the tomographic data used for calculation of the motion contrast data.

In the exemplary embodiments and modifications thereof described above, the acquisition unit 220 acquires the interference signal acquired in the imaging optical system 100 or Fourier-transformed data generated by the image generation unit 210, for example. However, the way in which the acquisition unit 220 acquires these signals is not limited to this. For example, the acquisition unit 220 may acquire these signals from a server or an imaging apparatus connected to the control unit 200 via a LAN, a WAN, the Internet or the like. Similarly, the acquisition unit 220 may acquire the noise signal, such as the background signal, of the imaging optical system 100 from a server or the like connected to the control unit 200 via a LAN or the like.

In the exemplary embodiments and modifications thereof described above, the spectral-domain OCT (SD-OCT) apparatus that uses an SLD as a light source has been described as the OCT apparatus. However, the OCT apparatus according to the present invention is not limited to this configuration. For example, the present invention can be applied to the OCT apparatus of any other type, such as the swept-source OCT (SS-OCT) apparatus that uses a swept-source light source capable of sweeping the wavelength of the emitted light.

In the exemplary embodiments and modifications thereof described above, a fiber optical system using a coupler as a splitting unit is used. However, a spatial optical system that uses a collimator and a beam splitter can also be used. The configuration of the imaging optical system 100 is not limited to the configuration described above, and some of the components of the imaging optical system 100 may be separate from the imaging optical system 100. In the exemplary embodiments and modifications thereof described above, the imaging optical system including the fundus observation system and the anterior eye portion observation system has been described. However, the imaging optical system for generating the OCTA image may not include these optical systems.

Furthermore, in the exemplary embodiments and modifications thereof described above, the subject to be inspected is a human eye. However, the target of the OCT imaging can be another organ or the like. In that case, the measurement optical system may include other components, such as an endoscope.

According to the present invention, a motion contrast image with higher contrast than when the conventional threshold processing is used can be provided.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™, a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2017-169235, filed Sep. 4, 2017, which is hereby incorporated by reference herein in its entirety.

What is claimed is:

1. An image processing apparatus, comprising:
at least one of (a) one or more processors and (b) circuitry, configured to function as:
a threshold calculation unit that calculates a threshold using a pixel value of a target pixel of one tomographic image of a plurality of tomographic images indicating tomographic information on substantially a same region of a subject to be inspected, wherein the plurality of tomographic images is used for generating a motion contrast image; and
a pixel value calculation unit that calculates a pixel value of the target pixel of the motion contrast image using a result of a comparison between the threshold and a pixel value of the target pixel of an other of the plurality of tomographic images.

2. An image processing apparatus comprising:
at least one of (a) one or more processors and (b) circuitry, configured to function as:
a threshold calculation unit that calculates a threshold using a pixel value of a target pixel of each of a plurality of tomographic images indicating tomographic information on substantially a same region of a subject to be inspected; and
a pixel value calculation unit that calculates a pixel value of the target pixel of a motion contrast image using a result of a comparison between the threshold and a motion contrast data calculated using a pixel value of the target pixel of each of the plurality of tomographic images,
wherein the threshold calculation unit
calculates first data $CI_1 = C_{ave} + \alpha \times \sqrt{C_{ave}}$ and second data $CI_2 = C_{ave} - \alpha \times \sqrt{C_{ave}}$ using an average value $C_{ave}$ of the pixel value of the target pixel of each of the plurality of tomographic images, a square root $\sqrt{C_{ave}}$ of the average value $C_{ave}$ and a coefficient $\alpha$, and
calculates the motion contrast data from the first data $CI_1$ and the second data $CI_2$ and designates the motion contrast data as the threshold.

3. The image processing apparatus according to claim 2, wherein the pixel value calculation unit sets the pixel value of the target pixel of the motion contrast image at 0 if the motion contrast data calculated using the pixel value of the target pixel of each of the plurality of tomographic images is equal to or smaller than the threshold, and calculates the pixel value of the target pixel of the motion contrast image using the motion contrast data if the motion contrast data is greater than the threshold.

4. The image processing apparatus according to claim 1, wherein in a two-dimensional coordinate system one coordinate axis of which indicates $I_1$ and the other coordinate axis of which indicates $I_2$, $I_1$ and $I_2$ being two pixel values at a same pixel location in the plurality of tomographic images, the threshold calculation unit calculates, as a first threshold $ths_{s1}$ and a second threshold $ths_{s2}$, two linear functions of the value $I_1$ with respect to value $I_2$ substantially in line symmetry with respect to a straight line passing through an origin of the two-dimensional coordinate system and inclined by 45° with respect to the coordinate axes, where $ths_{s2} < ths_{s1}$, and
the pixel value calculation unit sets the pixel value of the target pixel of the motion contrast image at 0 if a relation $ths_{s2} \leq I_2 \leq ths_{s1}$ is satisfied when the pixel value of the target pixel of the one tomographic image is substituted for $I_1$, and the pixel value of target pixel of the other of the plurality of tomographic images used for calculation of a motion contrast data is substituted for $I_2$, and calculates the pixel value of the target pixel of the motion contrast image from the motion contrast data if the relation $ths_{s2} \leq I_2 ths_{s1}$ is not satisfied.

5. The image processing apparatus according to claim 4, wherein the threshold calculation unit calculates, as the first threshold $ths_{s1}$ and the second threshold $ths_{s2}$, the following two linear functions of the value $I_1$ with respect to value $I_2$:

$$I_2 = I_1/\tan \gamma + I_0, \text{ and} \qquad ths_{s1}$$

$$I_2 = (I_1 - I_0) \tan \gamma, \qquad ths_{s2}$$

where $I_0$ denotes an intercept of the linear function of the second threshold $ths_{s2}$ on the $I_1$ coordinate axis, and $\gamma$ denotes an angle formed by the $I_1$ coordinate axis and the linear function of the second threshold $ths_{s2}$.

6. The image processing apparatus according to claim 1, wherein the threshold calculation unit further calculates a background threshold $thn = N_{ave} + \beta \times N_\sigma$ from (a) an average value $N_{ave}$ and a standard deviation $N_\sigma$ of a plurality of pieces of background data on an imaging optical system used for acquisition of the tomographic image on the subject to be inspected and (b) a coefficient $\beta$, and
the pixel value calculation unit further sets the pixel value of the target pixel of the motion contrast image at 0 using the background threshold $thn$ if pixel values $Ic_1$ and $Ic_2$ of the target pixel of the one tomographic image and the other of the plurality of tomographic images used for calculation of a motion contrast data satisfy a relation $Ic_1^2 + Ic_2^2 < thn^2$, and calculates the pixel value of the target pixel of the motion contrast image using the motion contrast data if the relation $Ic_1^2 + Ic_2^2 < thn^2$ is not satisfied.

7. The image processing apparatus according to claim 1, wherein the threshold calculation unit further calculates a background threshold $thn = Nave + \beta \times N_\sigma$ from (a) an average value $N_{ave}$ and a standard deviation $N_\sigma$ of a plurality of pieces of background data on an imaging optical system used for acquisition of the tomographic image on the subject to be inspected and (b) a coefficient $\beta$, and
the pixel value calculation unit further sets the pixel value of the target pixel of the motion contrast image at 0 using the background threshold $thn$ if all pixel values $Ic_1, Ic_2, \ldots, Ic_N$ of the target pixel of the plurality of tomographic images satisfy a relation $Ic_1^2 + Ic_2^2 + \ldots + Ic_N^2 < thn^2$, and calculates the pixel value of the target pixel of the motion contrast image using a motion contrast data if the relation $Ic_1^2 + Ic_2^2 + \ldots + Ic_N^2 < thn^2$ is not satisfied.

8. The image processing apparatus according to claim 5, wherein the threshold calculation unit further calculates a background threshold $thn = N_{ave} + \beta \times N_\sigma$ from (a) an average value $N_{ave}$ and a standard deviation $N_\sigma$ of the plurality of pieces of background data on an imaging optical system used for acquisition of the tomographic image on the subject to be inspected and (b) a coefficient $\beta$, and calculates the first threshold $ths_{s1}$ and the second threshold $ths_{s2}$ on the assumption that $I_0=thn$.

9. The image processing apparatus according to claim 1, the at least one of (a) one or more processors and (b) circuitry being configured to function as:
an image generation unit that calculates the approximate straight line $Ic_2=aIc_1+b$, and
a correction unit that corrects a magnitude of pixel value of the tomographic image,
wherein the correction unit corrects pixel value $Ic_2$ according to the following formula:

$$Ic_2'=\eta \times Ic_2,$$

where $Ic_1$ denotes one of pixel values of the target pixel of the one tomographic image and the other of the plurality of tomographic images, $Ic_2$ denotes the other of the pixel values, a denotes a lope of the line, b denotes a y-intercept of the line, and $\eta$ denotes a coefficient calculated from $Ic_1$, and $Ic_2$,
the threshold calculation unit calculates the threshold using pixel value $Ic_1$, and the corrected tomographic data value $Ic_2'$, and
the pixel value calculation unit calculates the pixel value of the target pixel of the motion contrast image using the threshold and a motion contrast data calculated using the pixel value $Ic_1$, and the corrected pixel value $Ic_2'$.

10. The image processing apparatus according to claim 9, wherein the correction unit
calculates an approximate straight line $Ic_2=aIc_1+b$, which is an approximation of sets of pixel value obtained by removing a distribution associated with background noise from a distribution of sets of pixel values used for calculation of the motion contrast data in a two-dimensional coordinate system whose coordinate axes indicate the two pixel values $Ic_1$, and $Ic_2$, and
calculates the coefficient $\eta$ according to $\eta 1/a$.

11. The image processing apparatus according to claim 1, wherein
the threshold calculation unit further calculates a high-value threshold $th_{hi}=N_{ave}+A \times N_{94}$ using (a) an average value $N_{ave}$ and a standard deviation $N_\sigma$ of the plurality of pieces of background data on an imaging optical system used for acquisition of the tomographic image on the subject to be inspected and (b) a coefficient A, and
the pixel value calculation unit further sets the pixel value of the target pixel of the motion contrast image at 0 using the high-value threshold $th_{hi}$ if pixel values $Ic_1$ and $Ic_2$ of the target pixel of the one tomographic image and the other of the plurality of tomographic images satisfy a relation $Ic_1^2+Ic_2^2>th_{hi}^2$, and calculates the pixel value of the target pixel of the motion contrast image using a motion contrast data if the relation $Ic_1^2+Ic_2^2>th_{hi}^2$ is not satisfied.

12. The image processing apparatus according to claim 1, wherein the threshold calculation unit sets a margin $\delta$ for the calculated threshold, and
the pixel value calculation unit calculates, as the pixel value of the target pixel of the motion contrast image, a motion contrast data multiplied by a weight w if the pixel value compared with the calculated threshold falls within a range of $\pm\delta$ with respect to the threshold.

13. The image processing apparatus according to claim 2, wherein the coefficient $\alpha$ ranges from 1 to 10.

14. The image processing apparatus according to claim 1, wherein the threshold calculation unit generates a mask that sets a pixel value at a pixel location associated with the target pixel of the motion contrast image at a value from 0 to 1 according to a result of comparison between the calculated threshold and the compared value, and
the pixel value calculation unit calculates the pixel value of the target pixel of the motion contrast image using the mask based on the threshold and a motion contrast data.

15. The image processing apparatus according to claim 1, wherein
the plurality of tomographic images is used for generating a plurality of motion contrast images, and
when taking an average of a plurality of motion contrast images in which the pixel value of the target pixel is calculated, the pixel value calculation unit omits the pixel value of the target pixel whose pixel value is set at 0 according to the threshold from the averaging processing for the plurality of motion contrast images.

16. An optical coherence tomography apparatus, comprising:
an imaging optical system that acquires a plurality of tomographic images indicating tomographic information on a subject to be inspected by performing optical coherence tomography of the subject to be inspected plural times using measuring light with which substantially a same region of the subject to be inspected is scanned, wherein the plurality of tomographic images is used for generating a motion contrast image; and
at least one of (a) one or more processors and (b) circuitry, configured to function as:
a threshold calculation unit that calculates a threshold using a pixel value of a target pixel of one tomographic image of the plurality of tomographic images acquired by the image optical system; and
a pixel value calculation unit that calculates a pixel value of the target pixel of a motion contrast image using a result of a comparison between the threshold and a pixel value of the target pixel of an other of the plurality of tomographic images.

17. The optical coherence tomography apparatus according to claim 16, wherein the threshold calculation unit calculates a background threshold $thn=N_{ave}+\beta \times N_{94}$ from (a) an average value $N_{ave}$ and a standard deviation $N_\sigma$ of a plurality of pieces of background data and (b) a coefficient $\beta$, and
the pixel value calculation unit sets the pixel value of the target pixel of the motion contrast image at 0 using the background threshold thn if pixel values $Ic_1$, and $Ic_2$, of the target pixel of the one tomographic image and the other of the plurality of tomographic images for which a motion contrast data is to be calculated satisfy a relation $Ic_1^2+Ic_2^2<thn^2$, and calculates the pixel value of the target pixel of the motion contrast image using the motion contrast data if the relation $Ic_1^2+Ic_2^2<thn^2$ is not satisfied.

18. An image processing method, comprising:
acquiring, at different times, a plurality of pieces of background data on an imaging optical system used for acquisition of two tomographic images indicating tomographic information on substantially a same region of a subject to be inspected, wherein the two tomographic images are used for generating a motion contrast image;
calculating a background threshold thn using the plurality of pieces of background data, and
based on the background threshold thn and pixel values $Ic_1$ and $Ic_2$ of target pixel of the two tomographic images, setting a pixel value of the target pixel of the motion contrast image at 0 if a relation $Ic_1^2+Ic_2^2<thn^2$ is satisfied, and calculating the pixel value of the target pixel of the motion contrast image using a motion contrast data generated using the two tomographic images if the relation $Ic_1^2+Ic_2^2<thn^2$ is not satisfied.

19. A non-temporary computer readable medium having stored thereon a program for causing, when being executed by a processor, the processor to perform each step of the image processing method of claim 18.

20. An image processing apparatus, comprising:
at least one of (a) one or more processors and (b) circuitry, configured to function as:
an acquisition unit that acquires, at different times, a plurality of pieces of background data on an imaging optical system used for acquisition of two tomographic images indicating tomographic information on substantially a same region of a subject to be inspected, wherein the two tomographic images are used for generating a motion contrast image;
a threshold calculating unit that calculates a background threshold thn using the plurality of pieces of background data, and
a pixel value calculation unit that, based on the background threshold thn and pixel values $Ic_1$, and $Ic_2$ of target pixel of the two tomographic images, sets a pixel value of the target pixel of the motion contrast image at 0 if a relation $Ic_1^2+Ic_2^2<thn^2$ is satisfied, and calculates the pixel value of the target pixel of the motion contrast image using a motion contrast data if the relation $Ic_1^2+Ic_2^2<thn^2$ is not satisfied.

21. The image processing apparatus according to claim 20, wherein the background threshold thn is calculated as $thn=N_{ave}+\beta \times N_\sigma$ using (a) an average value $N_{ave}$ and a standard deviation $N_\sigma$ of the plurality of pieces of background data and (b) a coefficient $\beta$.

22. The image processing apparatus according to claim 1, wherein the threshold calculation unit calculates two thresholds using the pixel value of the target pixel of the one tomographic image, and
the pixel value calculation unit calculates the pixel value of the target pixel of the motion contrast image as 0 if the pixel value of the target pixel of the other of the plurality of tomographic images is a value between the two thresholds.

23. An image processing method, comprising:
calculating a threshold using a pixel value of a target pixel of one tomographic image of a plurality of tomographic images indicating tomographic information on substantially a same region of a subject to be inspected, wherein the plurality of tomographic images is used for generating a motion contrast image; and
calculating a pixel value of the target pixel of the motion contrast image using a result of a comparison between the threshold and a pixel value of the target pixel of an other of the plurality of tomographic images.

24. A non-transitory computer-readable medium having stored thereon a program for causing, when being executed by a processor, the processor to perform each step of the image processing method of claim 23.

* * * * *